(12) United States Patent
Wang et al.

(10) Patent No.: US 9,943,373 B2
(45) Date of Patent: *Apr. 17, 2018

(54) EVALUATING PROSTHETIC HEART VALVE PLACEMENT

(71) Applicant: Henry Ford Health System, Detroit, MI (US)

(72) Inventors: Dee Dee Wang, Ypsilanti, MI (US); William O'Neill, Grosss Pointe Farms, MI (US); Eric Myers, Ferndale, MI (US); Michael Forbes, Dearborn, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/608,043

(22) Filed: May 30, 2017

(65) Prior Publication Data
US 2017/0258527 A1 Sep. 14, 2017

Related U.S. Application Data

(63) Continuation of application No. 14/965,057, filed on Dec. 10, 2015, now Pat. No. 9,693,830.
(Continued)

(51) Int. Cl.
*G06K 9/00* (2006.01)
*A61B 34/10* (2016.01)
(Continued)

(52) U.S. Cl.
CPC .......... *A61B 34/10* (2016.02); *G06F 19/3437* (2013.01); *A61B 34/25* (2016.02);
(Continued)

(58) Field of Classification Search
CPC .............. A61B 34/10; A61B 2034/105; A61B 2034/104; G06F 19/3437; A61F 2/24
(Continued)

(56) References Cited

U.S. PATENT DOCUMENTS 8,494,245 B2 7/2013 Liao et al.
8,666,714 B2 3/2014 Whirley et al.
(Continued)

FOREIGN PATENT DOCUMENTS

WO WO2013171039 A1 11/2013

OTHER PUBLICATIONS

Lang; Roberto M., et al.; Recommendations for Chamber Quantification; The European Society of Cardiology; Dec. 23, 2005, 30 pages; Published by Elsevier Ltd.*
(Continued)

*Primary Examiner* — Gregory F Cunningham
(74) *Attorney, Agent, or Firm* — Reising Ethington P.C.; Jeffrey L. Doyle

(57) ABSTRACT

A method for evaluating the placement of a prosthetic heart valve in a structure of interest. The method comprises acquiring one or more depictions of an anatomical region of interest that includes the structure of interest, wherein each depiction shows the structure of interest and/or the blood pool volume of the left ventricular outflow tract (LVOT) of the patient's heart. The method further comprises designating one or more positions in at least one of the one or more depictions wherein each position corresponds to a respective position in the structure of interest at which the prosthetic valve may be placed. The method still further comprises predicting, for each of the one or more designated positions, an amount of blood flow obstruction through the LVOT of
(Continued)

the patient's heart that would occur if the prosthetic valve was to be placed at a corresponding position in the structure of interest.

20 Claims, 16 Drawing Sheets

Related U.S. Application Data

(60) Provisional application No. 62/090,067, filed on Dec. 10, 2014.

(51) Int. Cl.
    *G06F 19/00*     (2018.01)
    *A61F 2/24*     (2006.01)
    *A61B 34/00*     (2016.01)

(52) U.S. Cl.
    CPC ... *A61B 2034/104* (2016.02); *A61B 2034/105* (2016.02); *A61F 2/24* (2013.01)

(58) Field of Classification Search
    USPC .......................................................... 382/100
    See application file for complete search history.

(56) References Cited

U.S. PATENT DOCUMENTS

| | | |
|---|---|---|
| 8,771,189 B2 | 7/2014 | Ionasec et al. |
| 8,775,133 B2 | 7/2014 | Schroeder |
| 9,693,830 B2 | 7/2017 | Wang et al. |
| 2007/0293734 A1 | 12/2007 | Coste-Maniere et al. |
| 2011/0153286 A1 | 6/2011 | Zaeuner et al. |
| 2012/0232386 A1 | 9/2012 | Mansi et al. |
| 2012/0323545 A1 | 12/2012 | Aulbach et al. |
| 2013/0073025 A1 | 3/2013 | Kassab |
| 2013/0129173 A1 | 5/2013 | Grbic et al. |
| 2013/0230225 A1 | 9/2013 | Waechter-Stehle et al. |
| 2015/0119692 A1 | 4/2015 | McHenry et al. |
| 2016/0038246 A1 | 2/2016 | Wang et al. |
| 2017/0084029 A1 | 3/2017 | Piazza et al. |

OTHER PUBLICATIONS

S/Iihalef; Viorel, et al.; Patient Specific Modelling of Whole Heart Anatomy, Dynamics and Haemodynamics from rour-Dimensional Cardia CT Images; Interface Focus; Mar. 23, 2011,12 pages.*

Litmanovich; Diana E., et al.; Imaging in Transcatheter Aortic Valve Replacement (TAVR): Role of the Radiologist; nsights Imaging; Jan. 21, 2014, 23 pages.*

Maslow, Andrew D., et al.; Echocardiographic Predictors of Left Ventricular Outflow Tract Obstruction and Systolic interior Motion of the Mitral Valve after Mitral Valve Reconstruction for Myxomatous Valve Disease; Journal of the American College of Cardiology; Aug. 30, 1999, 9 pages, vol. 34, No. 7; Published by Elsevier Science Inc.*

Maslow, Andrew D., et al.; Echocardiographic Predictors of Left Ventricular Outflow Tract Obstruction and Systolic Anterior Motion of the Mitral Valve after Mitral Valve Reconstruction for Myxomatous Valve Disease; Journal of the American College of Cardiology; Aug. 30, 1999, 9 pages, vol. 34, No. 7; Published by Elsevier Science Inc.

Tops; Laurens F., et al.; Noninvasive Evaluation of the Aortic Root with Multislice Computed Tomography, Implications for Transcatheter Aortic Valve Replacement; Journal of the American College of Cardiology; Dec. 16, 2007, 10 pages, vol. 1, No. 3; Published by Elsevier Science Inc.

Gijsen; Frank JH, et al.; Simulation of Stent Deployment in a Realistic Human Coronary Artery; Aug. 6, 2008, 11 pages; Published by BioMedical Engineering OnLine.

Schoenhagen; Paul, et al.; Three-Dimensional Imaging of the Aortic Valve and Aortic Root with Computed Tomography: New Standards in an Era of Transcatheter Valve Repair/Implantation; European Heart Journal; May 13, 2009, 8 pages; Published by the European Society of Cardiology.

Kurra; Vikram, et al.; Pre-Procedural Imaging of Aortic Root Orientation and Dimensions, Comparison Between X-Ray Angiographic Planar Imaging and 3-Dimensional Multidetector Row Computed Technology; The American College of Cardiology Foundation; Oct. 15, 2009, 9 pages, vol. 3, No. 1; Published by Elsevier Science Inc.

Schoenhagen; Paul, et al.; Three-Dimensional Imaging in the Context of Minimally Invasive and Transcatheter Cardiovascular Interventions using Multi-Detector Computed Tomography: From Pre-Operative Planning to Intra-Operative Guidance; European Heart Journal; Aug. 3, 2010, 15 pages; Published by the European Society of Cardiology.

Quaini; Annalisa, et al.; A Three-Dimensional Computational Fluid Dynamics Model of Regurgitant Mitral Valve Flow: Validation Against In Vitro Standards and 3D Color Doppler Methods; Cardivascular Engineering and Technology; Feb. 8, 2011, 13 pages.

Mihalef; Viorel, et al.; Patient Specific Modelling of Whole Heart Anatomy, Dynamics and Haemodynamics from Four-Dimensional Cardia CT Images; Interface Focus; Mar. 23, 2011, 12 pages.

Jelnin; Vladimir, et al.; Clinical Experience with Percutaneous Left Ventricular Transapical Access for Interventions in Structural Heart Defects, A Safe Access and Secure Exit; The American College of Cardiology Foundation; May 31, 2011, 7 pages, vol. 4, No. 8; Published by Elsevier Inc.

Jabbour; Andrew, et al.; Multimodality Imaging in Transcatheter Aortic Valve Implantation and Post-Procedural Aortic Regurgitation, Comparison Among Magnetic Resonance Cardiac Computed Tomography, and Echocardiography; The American College of Cardiology Foundation; Sep. 13, 2011, 9 pages, vol. 58, No. 21; Published by Elsevier Inc.

Schievano; Silvia, et al.; Finite Element Analysis to Study Percutaneous Heart Valves; UCL Institute of Cardiovascular Science; Mar. 30, 2012, 27 pages; Published by InTech.

Achenbach, Stephan, et al.; SCCT Expert Consensus Document on Computed Tomography Imaging Before Transcatheter Aortic Valve Implantation (TAVI)/Transcatheter Aortic Valve Replacement (TAVR); Journal of Cardiovascular Computed Tomography; Nov. 6, 2012, 15 pages.

Borazjani; Iman, et al.; Left Ventricular Flow Analysis: Recent Advances in Numerical Methods and Applications in Cardiac Ultrasound; Mar. 19, 2013, 12 pages; Hindawi Publishing Corporation.

Litmanovich; Diana E., et al.; Imaging in Transcatheter Aortic Valve Replacement (TAVR): Role of the Radiologist; Insights Imaging; Jan. 21, 2014, 23 pages.

Fast App: Looking Deep into Heart Valve Replacement; http://www.deskeng.com/de/fast-app-looking-deep-into-heart-valve-replacement; Feb. 12, 2014, 4 pages, accessed Oct. 31, 2014.

Guerrero; Mayra, et al.; First in Human Percutaneous Implantation of a Balloon Expandable Transcatheter Heart Valve in a Severly Stenosed Native Mitral Valve; Feb. 15, 2014, 5 pages.

Griffith; Boyce E.; Multi-Beat Simulations of the Fluid Dynamics of the Aortic Heart Valve with Physiological Driving and Loading Conditions using the Immersed Boundary Method; http://www.cims.nyu.edu/~griffith; Jul. 4, 2014, 14 pages, accessed Oct. 31, 2014.

McQueen; David M., et al.; Heart Animations Computed by the Immersed Boundary Method; http://www.math.nyu.edu/faculty/peskin/myo3D/index.html; Copyright 2005, 2 pages, accessed Oct. 31, 2014.

University of California, Health Sciences; Doctors use 3D Printed Model to Guide Tricky Heart Valve Replacement; ScienceDaily; Jul. 1, 2015, 3 pages.

* cited by examiner

EVALUATING PROSTHETIC HEART VALVE PLACEMENT

CROSS REFERENCE TO RELATED APPLICATIONS

This application is a continuation of U.S. patent application Ser. No. 14/965,057 filed on Dec. 10, 2015, which claims the benefit of U.S. Provisional Patent Application No. 62/090,067 filed Dec. 10, 2014. The entire contents of both of the aforementioned applications are incorporated herein by reference.

TECHNICAL FIELD

This disclosure relates generally to prosthetic heart valves, and more particularly to periprocedurally evaluating the placement of a prosthetic heart valve, such as, for example and without limitation, a prosthetic mitral valve, in a given structure of interest.

BACKGROUND

Non-invasive percutaneous implantation of prosthetic devices, for example, heart valves, poses certain challenges to physicians. As opposed to surgically invasive procedures, such as, for example, open heart surgery, physicians performing non-invasive percutaneous implantation procedures have a limited field of view and are generally limited to the use of images generated by two-dimensional (2D) imaging modalities (e.g., fluoroscopy, ultrasound, etc.) during the procedure. Accordingly, periprocedural planning for non-invasive procedures that involves advanced imaging strategies can lead to more successful percutaneous implantation outcomes.

In the field of cardiology, transfemoral, transapical, and transaortic implantation are promising alternatives to open heart surgery, particularly for inoperable and high surgical risk patients. However, because physicians are typically limited to 2D imaging during the procedure itself, proper planning and evaluation is required to accurately assess and determine, for example, the placement of the prosthetic device within the structure in which the prosthetic device is being implanted that is ideal or optimal for that particular patient. Additionally, as it relates to transcatheter mitral valve replacement (TMVR), conventional transcatheter prosthetic heart valves are not specifically designed for mitral position implantation and have intrinsic geometry that may present challenges to mitral implantation. For example, such heart valves may present challenges as it relates to left ventricular outflow tract (LVOT) obstruction.

SUMMARY

According to one embodiment, there is provided a computer-implemented method for evaluating the placement of a prosthetic mitral heart valve in a structure of interest located in the heart of a patient. The method comprises acquiring one or more depictions of an anatomical region of interest that includes the structure of interest, wherein each of the one or more depictions shows the structure of interest, the blood pool volume of the left ventricular outflow tract (LVOT) of the patient's heart, or both. The method further comprises designating one or more positions in at least one of the one or more depictions, wherein each position corresponds to a respective position in the structure of interest at which the prosthetic valve may be placed. The method still further comprises predicting, for each of the one or more positions, an amount of blood flow obstruction through the LVOT of the patient's heart that would occur if the prosthetic valve was to be placed at a corresponding position in the structure of interest.

According to another embodiment, there is provided a computer-implemented method for evaluating the placement of a prosthetic mitral heart valve in a structure of interest located in the heart of a patient. The method comprises acquiring a depiction of an anatomical region of interest that includes the structure of interest, wherein the depiction shows the structure of interest and the blood pool volume of the LVOT of the patient's heart. The method further comprises importing one or more models of the prosthetic valve into the acquired depiction of the structure of interest. The method still further comprises predicting, for each of the one or more positions of the one or more models of the prosthetic valve, an amount of blood flow obstruction through the LVOT of the patient's heart that would occur if the prosthetic valve was to be placed at a corresponding position in the structure of interest.

According to yet another embodiment there is provided a computer-implemented method for evaluating the placement of a prosthetic mitral heart valve in a structure of interest located in the heart of the patient. The method comprises acquiring a plurality of images of an anatomical region of interest that includes the structure of interest, wherein each of the plurality of images shows the structure of interest, the blood pool volume of the LVOT of the patient's heart, or both. The method further comprises designating a position in at least one of the one or more images that corresponds to a position in the structure of interest at which the prosthetic valve may be placed. The method still further comprises predicting an amount of blood flow obstruction through the LVOT of the patient's heart that would occur if the prosthetic valve was to be placed at a position in the structure of interest that corresponds to the position designated in the at least one of the one or more images.

BRIEF DESCRIPTION OF DRAWINGS

One or more embodiments of the invention will hereinafter be described in conjunction with the appended drawings, wherein like designations denote like elements, and wherein.

DETAILED DESCRIPTION

The system and method described herein can assist physicians in pre-operational planning and post-operative evaluation (also referred to as "periprocedural planning") of percutaneous procedures, for example, procedures involving the implantation of prosthetic heart valves. Generally, the system and method described herein use advanced imaging and modeling strategies to accurately assess the placement or positioning of a prosthetic valve in a structure of interest, and to determine an ideal or optimal position of the prosthetic valve in the structure of interest that is specific to the particular patient on which the procedure is to be performed. Although the system and method may be applicable to planning for and evaluating a variety of procedures, they are particularly applicable to procedures involving the mitral heart valve, and the implantation of a prosthetic mitral valve, in particular. Accordingly, the description below will be primarily with respect to the evaluation of the placement of a prosthetic mitral valve. It will be appreciated, however, that various teachings set forth herein could also be applied to any number of other procedures, and thus, the present disclosure is not intended to be limited to the use of the system and method described herein for any particular type(s) of procedure(s).

Figure 1:
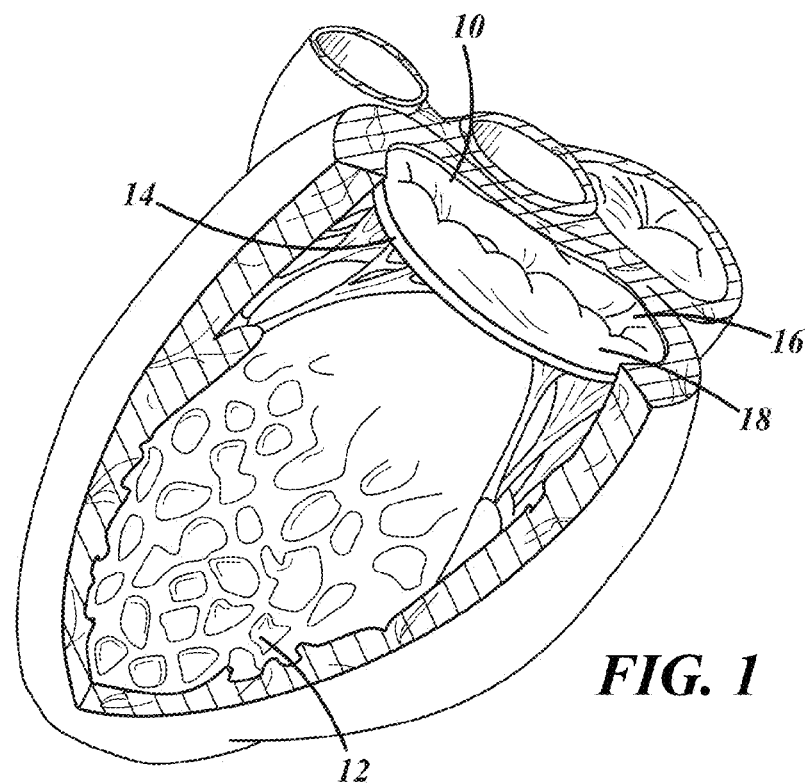
FIG. 1 is a schematic and diagrammatic view a portion of the human heart.
Figure 2:
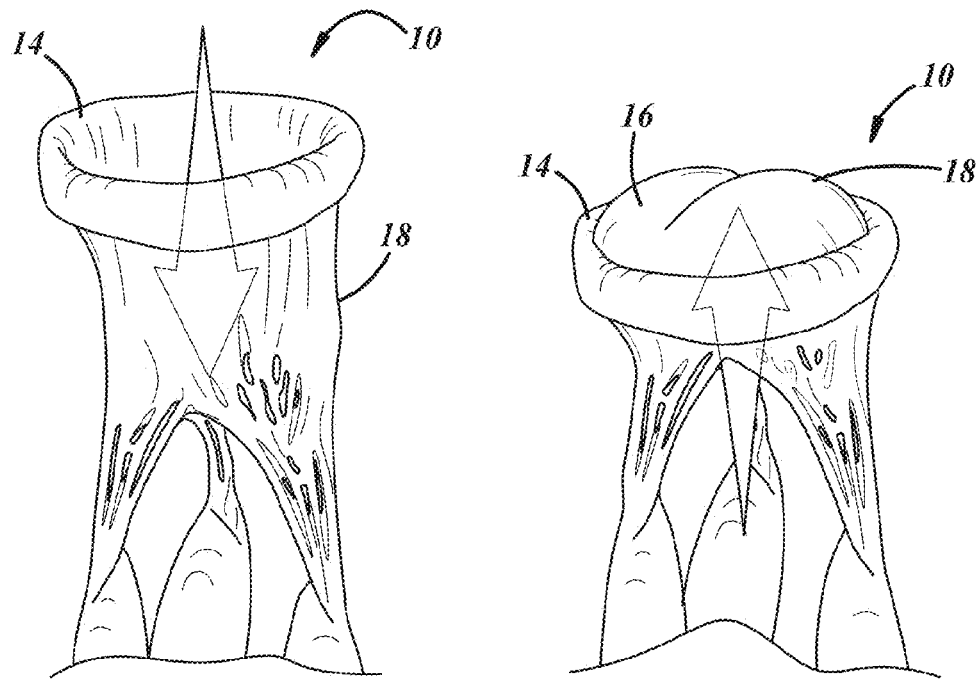
FIG. 2 is a schematic and diagrammatic view of the mitral valve of a human heart showing the operation of the mitral valve.

For purposes of context, FIGS. 1 and 2 depict a native mitral valve 10. The mitral valve 10 is disposed between the left atrium (not shown) and the left ventricle 12, and is configured to control or regulate the blood flow from the left atrium to the left ventricle. More specifically, as the mitral valve opens, an asymmetric toroidal vortex forms during the early diastolic phase of the cardiac cycle as blood flows from the left atrium to the left ventricle. The unique saddle shape of the annulus 14 of the mitral valve 10 changes during the cardiac cycle, and is at its largest in the diastolic phase when the valve is open, and is at its smallest in the systolic phase when the valve is closed. Unlike the aortic valve which is gated by three leaflets, the mitral valve is gated by two leaflets: an anterior leaflet 16 and a posterior leaflet 18. In at least some embodiments, determining an optimal or ideal placement of a prosthetic mitral valve requires an accurate evaluation or assessment of the annulus 14 (also referred to herein as "mitral annulus").

Figure 3:
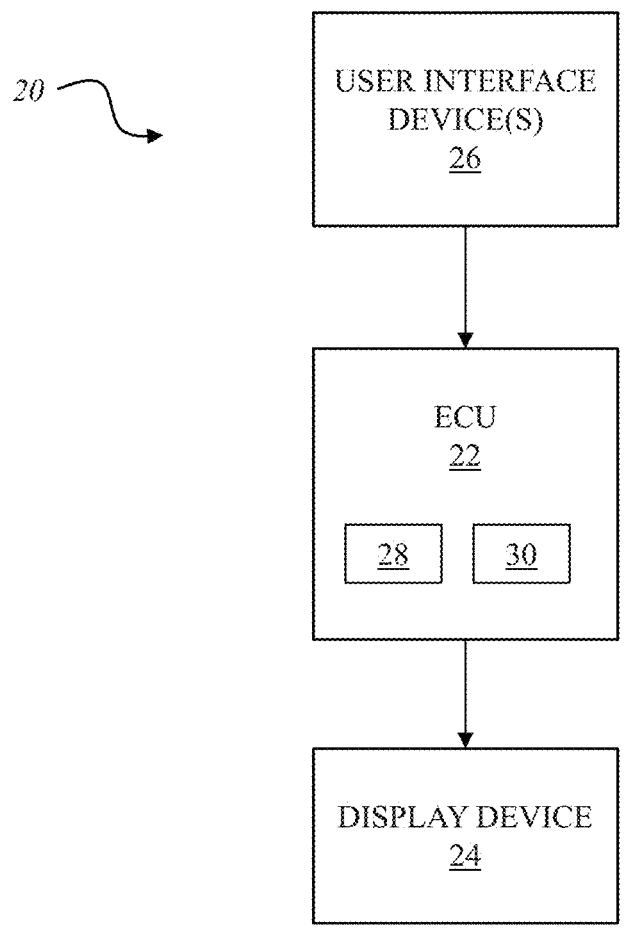
FIG. 3 is a schematic and block diagram of an illustrative embodiment of a system for performing one or more embodiments of the methodology described herein.

FIG. 3 depicts an illustrative embodiment of a system 20 for evaluating the placement of a prosthetic device in a structure of interest located in an anatomical region of interest of a patient's body. In an embodiment, the prosthetic device is a prosthetic heart valve (e.g., a prosthetic mitral valve) and the anatomical region of interest is at least a region of the patient's heart. In the illustrative embodiment, the system 20 comprises, among potentially one or more other components, an electronic control unit (ECU) 22, a display device 24, and one or more user interface devices 26.

The ECU 22 may comprise one or more electronic processing units 28 and one or more electronic memory devices 30, as well as, for example, input/output (I/O) devices and/or other known components. In another embodiment, rather than the ECU 22 comprising the memory device 30, the system 20 may include one or more memory devices 30 that are separate and distinct from the ECU 22 (and the processing unit(s) 28 thereof, in particular) but that is/are accessible thereby.

The processing unit(s) 28 of the ECU 22 may include any type of suitable electronic processor (e.g., a programmable microprocessor or microcontroller, an application specific integrated circuit (ASIC), etc.) that is configured to execute appropriate programming instructions for software, firmware, programs, algorithms, scripts, etc., to perform various functions, such as, for example and without limitation, one or more steps of the methodology described herein.

The memory device(s) 30, whether part of the ECU 22 or separate and distinct therefrom, may include any type of suitable electronic memory means and may store a variety of data and information. This includes, for example, software, firmware, programs, algorithms, scripts, and other electronic instructions that, for example, are required to perform or cause to be performed one or more of the functions described elsewhere herein (e.g., that are used (e.g., executed) by ECU 22 (and the processing unit(s) 28 thereof, in particular) to perform various functions described herein). Alternatively, rather than all of the aforementioned information/data being stored in a single memory device, in an embodiment, multiple suitable memory devices may be provided. These are, of course, only some of the possible arrangements, functions and capabilities of ECU 22, as others are certainly possible. In any event, in at least some embodiments, the memory device 30 may comprise a computer program product, or software, that may comprise or include a non-transitory, computer-readable storage medium. This storage medium may have instructions stored thereon that may be used to program a computer system (or other electronic devices, for example, the ECU 22) to implement the control of some or all of the functionality described herein. A computer-readable storage medium may include any mechanism for storing information in a form (e.g., software, processing application) readable by a machine (e.g., a computer, processing unit, etc.). The computer-readable storage medium may include, but is not limited to, magnetic storage medium (e.g., floppy diskette); optical storage medium (e.g., CD-ROM); magneto optical storage medium; read only memory (ROM); random access memory (RAM); erasable programmable memory (e.g., EPROM and EEPROM); flash memory; or electrical or other types of medium suitable for storing program instructions. In addition, program instructions may be communicated using optical, acoustical, or other form of propagated signal (e.g., carrier waves, infrared signals, digital signals, or other types of signals or mediums).

The display device 24 may comprise any number of display devices known in the art, for example and without limitation, liquid crystal display (LCD), cathode ray tube (CRT), plasma, or light emitting diode (LED) monitors or displays. The display device 24 is electrically connected or coupled to the ECU 22 and is configured to be controlled by the ECU 22 such that images or models of, for example, anatomical structures generated or obtained by the ECU 22, including those used in performing the method described below, may be displayed thereon and may be used for the purposes described herein. Additionally, in an embodiment wherein the ECU 22 may be configured to generate an interactive graphical user interface (GUI) that allows, for example, a physician to manipulate images or models displayed on the display device (e.g., removing layers of a model, moving models, etc.), facilitate the taking of measurements, etc., the display device 24 may also display such a GUI. In any event, the display device 24 is configured to receive electrical signals from the ECU 22 and to display content represented by the received signals which may be viewed by, for example, a physician.

The user interface device(s) 26 may comprise any number of suitable devices known in the art. For example, and without limitation, the user input device(s) 26 may comprise one or a combination of a touch screen (e.g., LCD touch screen), a keypad, a keyboard, a computer mouse or roller ball, and/or a joystick, to cite a few possibilities. In certain implementations, the display device 24 and user input device 26 may be combined together into a single device. Regardless of the particular form the user interface device(s) take, the user input device(s) 26 may be electrically connected or coupled (e.g., via wired or wireless connections) to the ECU 22, and are configured to facilitate a measure of communication between a user (e.g., physician) and the system 20, and the ECU 22 thereof, in particular. More particularly, the user interface device(s) 26 may allow a physician to manipulate images or models displayed on the display device 24 (e.g., rotate images/models, strip away or add layers to a model/image, move models relative to each other, import one model/image into another model/image, section portions of a model/image, etc.), to take or command the taking of desired measurements of anatomical structures represented by or in the images or models displayed on the display device 24, etc.

While certain components of the system 20 have been described above, it will be appreciated that in some implementations, the system 20 may include more or fewer components than are included in the arrangement described above. Accordingly, the present disclosure is not intended to be limited to any particular implementation(s) or arrangement(s) of the system 20.

Figure 4:
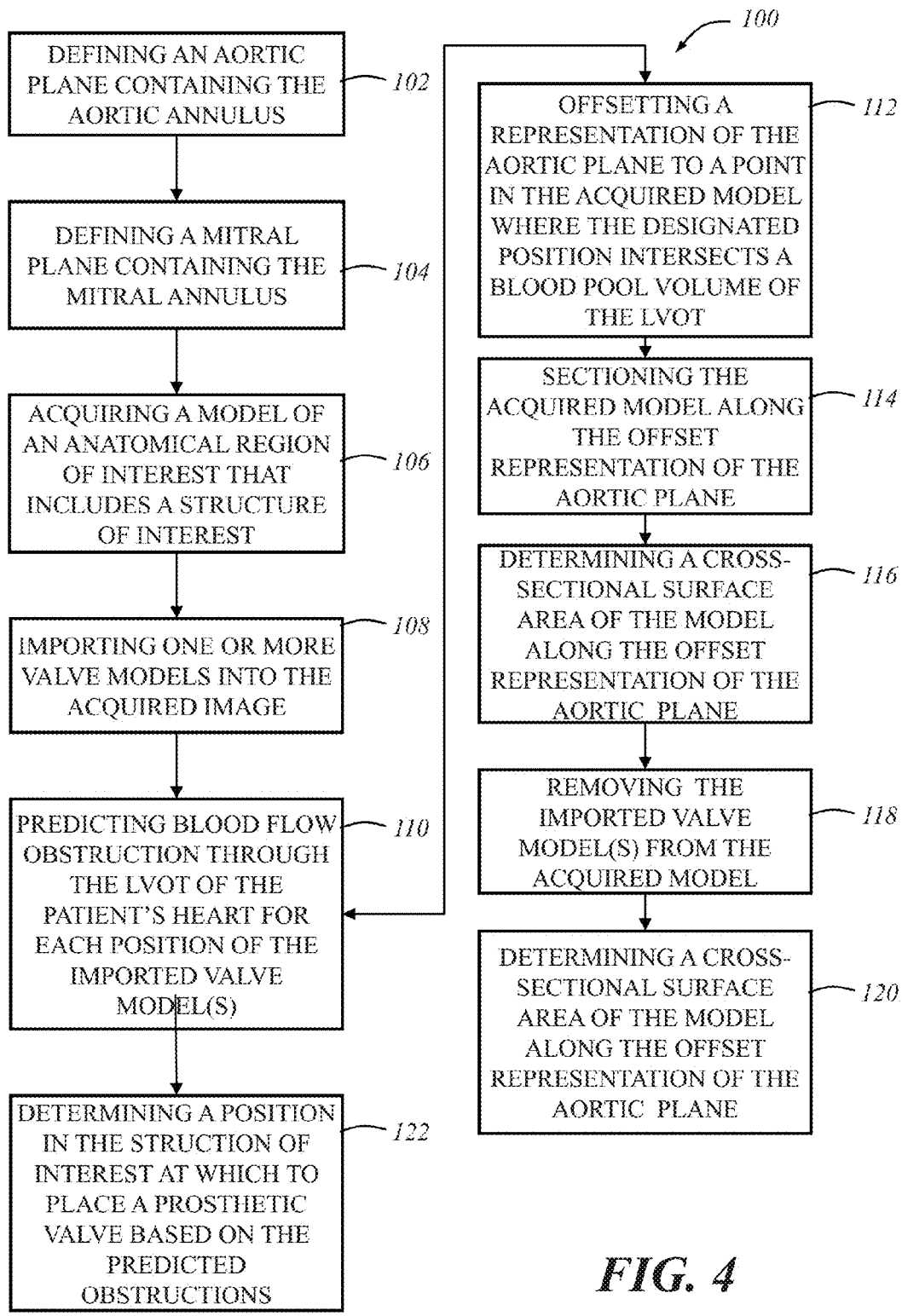
FIG. 4 is a flowchart of an illustrative embodiment of a method that may be used to evaluate prosthetic heart valve placement.

Turning now to FIG. 4, there is shown an illustrative embodiment of a method (method 100) for evaluating the placement of an implantable prosthetic device within a structure of interest located an anatomical region of a patient's body. The prosthetic device may be, for example, a prosthetic heart valve, and in an embodiment, a prosthetic mitral heart valve; and thus, in an embodiment, the anatomical region in which the structure of interest is located may at least partially include the patient's heart (or at least a portion thereof, for example, one or more of the left ventricle, the left atrium, and the LVOT of the patient's heart). For purposes of illustration, the description below will be primarily with respect to evaluating the placement of a prosthetic mitral heart valve. It will be appreciated, however, that the methodology described herein may be used to evaluate the placement of other prosthetic devices.

In at least some embodiments, all of the steps of method 100 may be performed or carried out by an appropriately or suitably configured system, for example and without limitation, the system 20 described above, either alone or in conjunction with input from a user (e.g., physician). In other embodiments, however, some, but not all, of the steps may be performed or carried out by different systems such that certain steps may be performed by one system (e.g., system 20), and other steps may be performed by one or more other suitable systems. For purposes of illustration, the description below will be primarily with respect to an embodiment wherein the method 100 is performed by the system 20 described above either alone or in conjunction with user input. It will be appreciated, however, that the present disclosure is not limited to such an embodiment. Additionally, it will be appreciated that unless otherwise noted, the performance of method 100 is not meant to be limited to any one particular order or sequence of steps, or to any particular component(s) for performing the steps.

In an embodiment, method 100 includes a step 102 of defining a plane that contains the aortic annulus of the patient's heart, hereinafter referred to as the "aortic plane." Step 102 may be performed using any number of techniques known in the art. In one embodiment, however, step 102 comprises acquiring image data relating to an anatomical region of the patient's heart that includes at least portions of the left ventricle, left atrium, and aorta of the patient's heart. In an illustrative embodiment, the image data comprises computed tomography (CT) image data, and more particularly, two-dimensional (2D) CT data. It will be appreciated, however, that in other embodiments, the image data may comprise data acquired using an imaging modality other than CT, for example, magnetic resonance imaging (MRI), echocardiogram imaging, or another suitable imaging modality. Accordingly, the present disclosure is not intended to be limited to any particular type of image data; however, for purposes of illustration and clarity, the description below will be primarily with respect to an embodiment wherein CT image data is used. Additionally, in an embodiment, image data may be acquired for both the diastolic and systolic phases of the patient's cardiac cycle, and in such as embodiment, the aortic plane may be defined for each phase.

Figure 5:
FIG. 5 is an computed tomography (CT) image of the aortic annulus of a patient that may be used, for example, in the performance of one or more steps of the method illustrated in FIG. 4.
Figure 6:
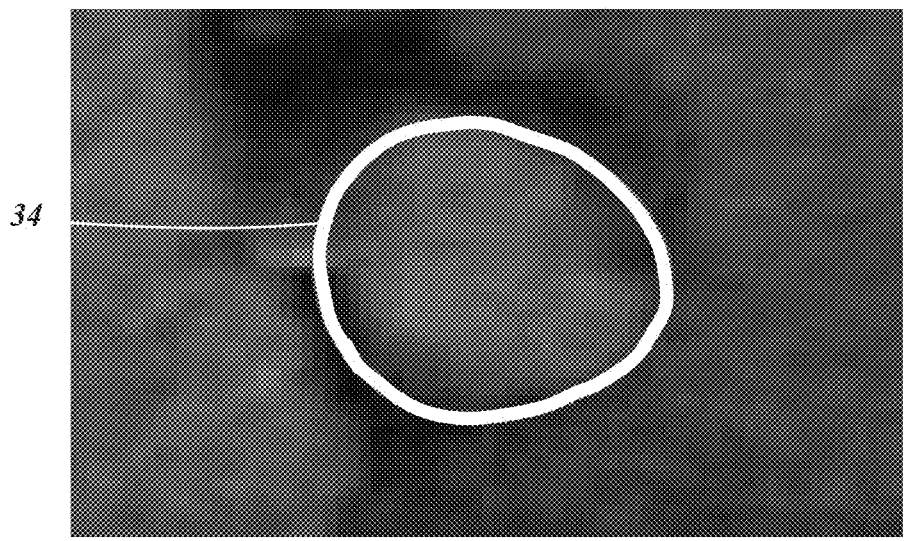
FIG. 6 is a CT image of the aortic annulus shown in FIG. 5 with a spline disposed thereon representing the aortic annulus and a plane containing the aortic annulus.

In any event, in an embodiment, one or more 2D images or views generated or produced from the acquired CT image data may be used to define the aortic plane. More particularly, a 2D image may be used to define a certain number of points (e.g., three (3) points) that may be used to define the aortic plane. In an embodiment, one or more predetermined landmarks (e.g., anatomical landmarks) may be used to define the plane-defining points. In one such embodiment, the predetermined landmarks may comprise the cusps of the aortic valve. FIG. 5 depicts a 2D CT image in which three points 32a, 32b and 32c each corresponding to an aortic valve cusp are defined. Regardless of the landmarks used, the plane-defining points may be defined or identified in a number of ways. In one embodiment, the points may be defined automatically by the ECU 22 of the system 20 (e.g., by the processing unit 28 of the ECU 22) using suitable image processing software/techniques. In other embodiments, the points may be defined by a user (e.g., physician). More specifically, the 2D image may be displayed on the display device 24 and the user may define the plane-defining points using the user interface device(s) 26 of the system 20. For example, the user may manipulate a mouse device to move a cursor to a desired location in the displayed image and to "click" the mouse to define a point. In any event, once the plane-defining points are defined, a plane containing all of the defined points can be defined as the aortic plane. In at least some embodiments, the aortic plane can be represented on a 2D image by a spline 34 representative of the aortic annulus, which may be displayed on the display device 24 as shown in FIG. 6. While certain techniques or implementations for defining the aortic plane-defining points, and thus, defining the aortic plane itself have been provided above, it will be appreciated that any suitable technique(s) for doing so may be used. Accordingly, the present disclosure is not intended to be limited to any particular technique(s) for doing so.

In an embodiment, the method 100 further includes a step 104 of defining a plane that contains the mitral annulus of the patient's heart, hereinafter referred to as the "mitral plane." As with step 102, step 104 may be performed using any number of techniques known in the art. For example, in one embodiment, step 104 comprises acquiring image data relating to an anatomical region of the patient's heart that includes at least portions of the left ventricle, left atrium, and aorta of the patient's heart. This image data may be the same image data acquired in step 102 or may comprise different image data. In either instance, the image data may comprise CT image data, and more particularly, 2D CT data. It will be appreciated, however, that in other embodiments, the image data may comprise data acquired using an imaging modality other than CT, for example, MRI, echocardiogram, or another suitable imaging modality. Accordingly, the present disclosure is not intended to be limited to any particular type of image data; however, for purposes of illustration and clarity, the description below will be primarily with respect to an embodiment wherein CT image data is used. Additionally, in an embodiment, image data may be acquired for both the diastolic and systolic phases of the patient's cardiac cycle, and in such as embodiment, the mitral plane may be defined for each phase.

Figure 7:
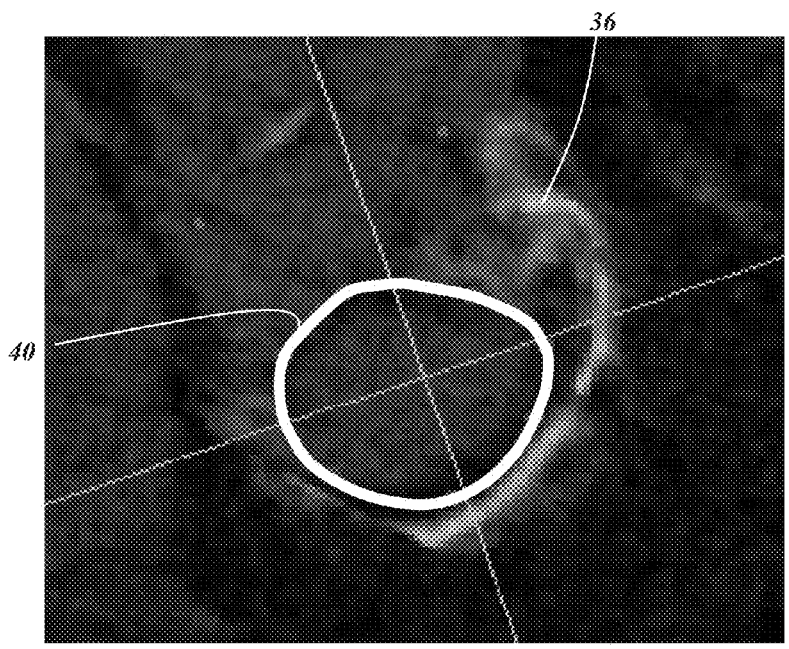
FIG. 7 is a CT image of the mitral annulus of a patient that may be used, for example, in the performance of one or more steps of the method illustrated in FIG. 4, wherein the image has a spline disposed thereon representing the mitral annulus and a plane containing the mitral annulus.
Figure 8:
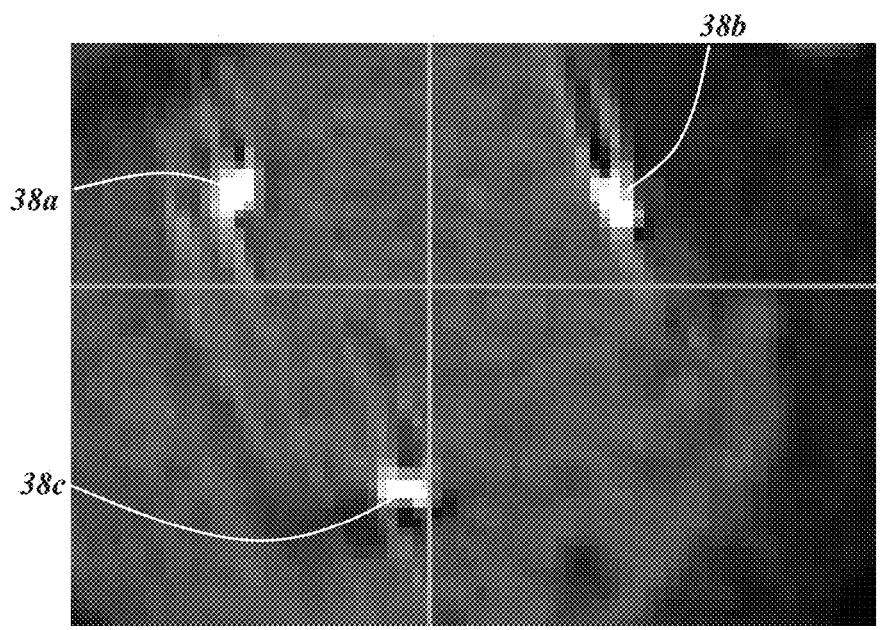
FIG. 8 is CT image of a portion of a previously-implanted prosthetic mitral valve that may be used, for example, in the performance of one or more steps of the method illustrated in FIG. 4, wherein he image shows markers or landmarks that may be used for performing the method.
Figure 9:
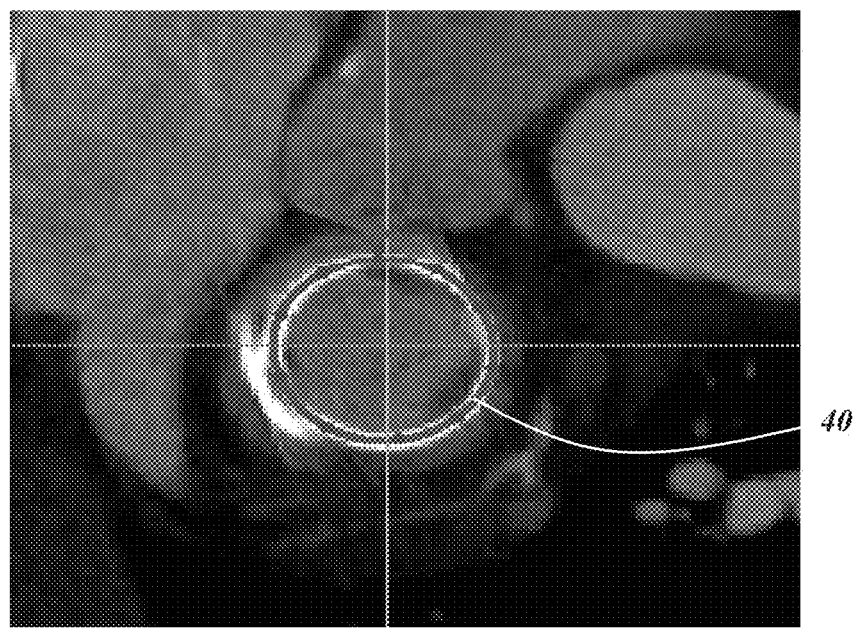
FIG. 9 is a CT image of the mitral annulus that may be used, for example, in the performance of one or more steps of the method illustrated in FIG. 4, wherein the image has a spline disposed thereon representing the mitral annulus and a plane containing the mitral annulus.

In any event, in an embodiment, one or more 2D images generated from the acquired CT image data may be used to define the mitral plane. More particularly, a 2D image may be used to define a certain number of points (e.g., three (3) points) that may be used to define the mitral plane. In an embodiment, one or more predetermined landmarks (e.g., anatomical landmarks) may be used to define the plane-defining points. The particular landmarks used may depend, at least in part, on the nature of the structure of interest into which the prosthetic valve is to be implanted. For example, in an instance wherein the structure of interest is a native mitral valve, the landmarks may include areas of calcification and/or leaflet tips and/or insertion points at the mitral annulus of the native valve, to cite few possibilities. In an instance wherein the structure of interest comprises a previously-implanted device or object, for example, a mitral ring, the landmarks may comprise that device or at least certain portions thereof. An example of such an instance is shown in FIG. 7 wherein a previously-implanted mitral ring 36 is shown in a 2D CT image. Finally, in an instance wherein the structure of interest comprises a previously-implanted prosthetic mitral valve (i.e., for a "valve-in-valve" procedure wherein a second prosthetic valve is implanted within a first, previously-implanted prosthetic valve), the landmarks may comprise portions of the previously-implanted valve, for example, the tips of the struts of the previously-implanted valve. An example of this instance is shown in FIG. 8, which depicts a 2D CT image in which three points 38a, 38b and 38c, each corresponding to a strut tip of a previously-implanted prosthetic mitral valve, are defined. In any event, the plane-defining points may be defined or identified in a number of ways. In one embodiment, the points may be defined automatically by the ECU 22 of the system 20 (e.g., by the processing unit 28 of the ECU 22) using suitable image processing software/techniques. In other embodiments, the points may be defined by a user (e.g., physician). More specifically, the 2D image may be displayed on the display device 24 and the user may define the plane-defining points using the user interface device(s) 26 of the system 20. For example, the user may manipulate a mouse device to move a cursor to a desired location in the image and to "click" the mouse to define a point. In any event, once the plane-defining points are defined, a plane containing all of the defined points can be defined as the mitral plane. In at least some embodiments, the mitral plane can be represented on a 2D image by a spline 40 representative of the mitral annulus, which may be displayed on the display device 24 as shown in FIG. 9. While certain techniques or implementations for defining the mitral plane-defining points, and thus, defining the mitral plane itself have been provided above, it will be appreciated that any suitable technique(s) for doing so may be used. Accordingly, the present disclosure is not intended to be limited to any particular technique(s) for doing so.

In an embodiment, the performance of steps 102 and 104 may be facilitated at least in part by software stored in, for example, the memory device 30 of the system 20. In an embodiment, this software may comprise a software program commercially available from Materialise NV under the name Mimics®; though any other suitable software may certainly be used instead. In an embodiment, each of the defined aortic and mitral planes (i.e., the splines 34, 40 representative thereof, respectively) may be exported as, for example, an .IGES file, and may be used as will be described below.

Once the aortic and mitral planes are defined in steps 102 and 104, respectively, method 100 may comprise a step 106 of acquiring one or more depictions of an anatomical region of interest of the patient's body that includes the structure of interest, and wherein each of the one or more depictions shows the structure of interest, the blood pool volume of the left ventricular outflow tract (LVOT) of the patient's heart, or both. In an embodiment, the one or more depictions comprise one or more computer-generated models of the anatomical region of interest, for example, one or more three-dimensional (3D) models. For purposes of illustration and clarity, the description below will be with respect to an embodiment wherein the acquired depiction(s) comprise a 3D model of the anatomical region of interest showing the structure of interest and the blood pool volume of the LVOT. It will be appreciated, however, that in other embodiments, multiple depictions in the form of two or more computer-generated models each showing the structure of interest, the LVOT blood pool volume, or both may be acquired and used in the manner to be described below.

In an embodiment where a single 3D model is acquired in step 106, that model may be acquired in a number of ways. One way is by obtaining a previously-generated model from a memory device, for example, the memory device 30 of the system 20. Another way is by generating the model from image data, for example 2D image data. In the latter instance, the image data may be the same image data acquired in step 102 and/or step 104, or alternatively, may be other image data (e.g., 2D CT image data) acquired as part of step 106. In either instance, the model may be generated using techniques well known in the art, such as, for example, that or those techniques described in U.S. patent application Ser. No. 14/820,617 filed on Aug. 7, 2015, the entire contents of which are incorporated herein by reference; and in an embodiment, may be generated by, for example, the ECU 22 of the system 20, and the processing unit 28 thereof, in particular. Accordingly, it will be appreciated that the present disclosure is not intended to be limited to any particular way(s) of acquiring the one or more depictions in step 106.

Regardless of how the one or more depictions is/are acquired in step 106, in an embodiment, the acquired depictions (e.g., the single 3D model) may be copied into or used by a suitable software program for performing the steps below. An example of such software is that commercially available from Materialise NV under the name 3-Matic STL. Representations of the aortic and mitral planes defined respectively in steps 102 and 104 may also be imported into the model acquired in step 106.

Figure 10A:
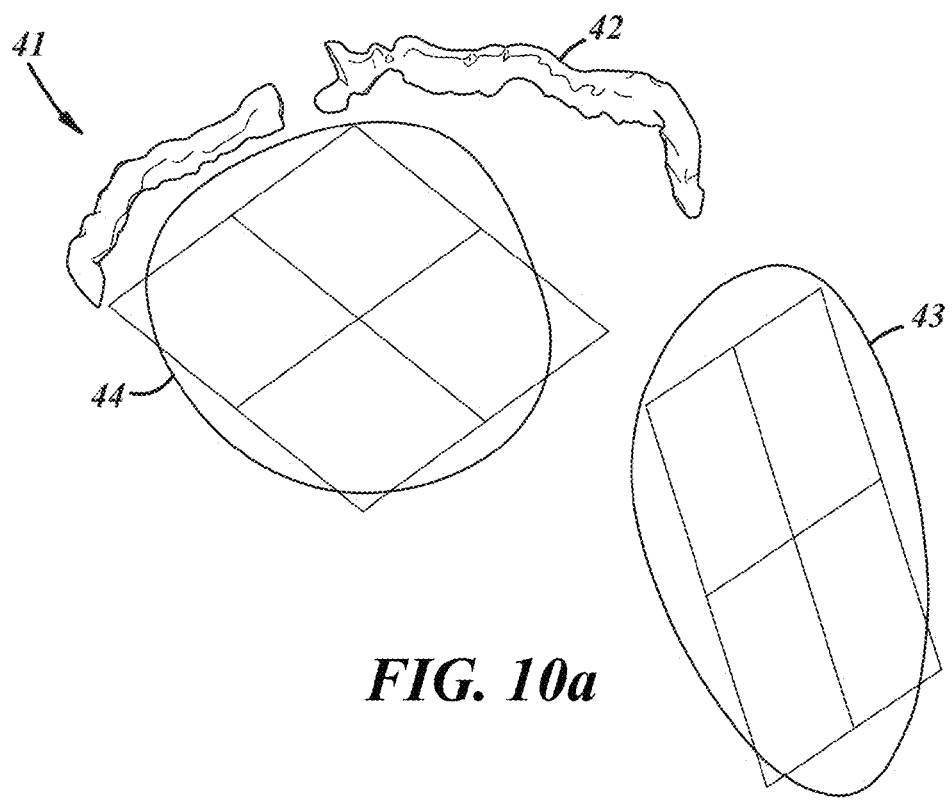
FIGS. 10a-10e are depictions of models that may be used in the performance of the method illustrated in FIG. 4, and showing an illustrative embodiment of how the method illustrated in FIG. 4 is carried out.

To better illustrate, FIG. 10*a* depicts a portion of a model 41 acquired in step 106 that includes or shows a model of a structure of interest 42 in the nature of a previously-implanted mitral ring, along with representations 43, 44 of the aortic and mitral planes, respectively (which, in an embodiment, may comprise splines 34, 40 representing the aortic and mitral planes, respectively). As shown in FIG. 10*a*, in an embodiment, the splines 34, 40 representing the aortic and mitral planes may have datum planes fit to the origins thereof using, for example, a "fit plane" operation to define or generate the representations 43, 44 of the aortic and mitral planes. It will be appreciated that in an embodiment, the model 41 may also show or include a model of the LVOT blood pool volume. In at least certain embodiments, the blood pool volume portion of the model 41 may be "hidden" such that it is not always visible, which is the case in the embodiment shown in FIG. 10*a*.

Figure 11A:
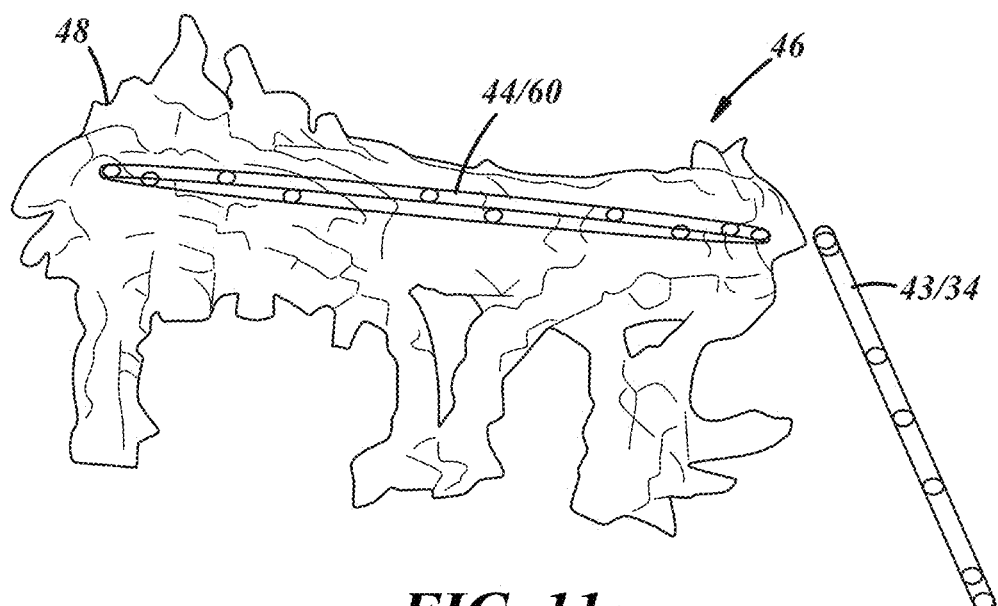
FIGS. 11a-11e are depictions of models that may be used in the performance of the method illustrated in FIG. 4, and showing an illustrative embodiment of how the method illustrated in FIG. 4 is carried out.

FIG. 11*a* also depicts an embodiment wherein at least a portion of a model 46 acquired in step 106 that includes or shows a model of a structure of interest 48 in the nature of a previously-implanted prosthetic mitral valve, along with representations 43, 44 of the aortic and mitral planes (which, in an embodiment, may comprise splines 34, 40 representing the aortic and mitral planes, respectively). As with FIG. 10*a* described above, it will be appreciated that in an embodiment, the model 46 may also show or include a model of the LVOT blood pool volume. In at least certain embodiments, the blood pool volume portion of the model 46 may be "hidden" such that it is not always visible, which is the case in the embodiment shown in FIG. 11*a*.

In any event, in at least some implementations, the placement of the representations of the aortic and mitral planes relative to the acquired model is controlled entirely by the software program, and the locations at which the representations are placed correspond at least generally to the actual locations of the aortic and mitral annuli of the patient's heart relative to the structure of interest and/or the LVOT of the patient's heart. Additionally, in at least some implementations, at least a portion of the model acquired in step 106 and the representations 43, 44 of one or both of the aortic and mitral planes may be displayed on, for example, the display device 24 of the system 20, for a user of the system 10 to view.

In an embodiment, following the acquisition of depiction(s) step 106 and the incorporation of the representations 43, 44 of the aortic and mitral planes therewith, method 100 may move to a step 108 of designating one or more positions in at least one of the acquired depictions (e.g., 3D model) showing the structure of interest, wherein each designated position corresponds to a respective position or location in the structure of interest at which the prosthetic valve may be placed. In an embodiment, step 108 comprises importing one or more models or other representations of a prosthetic valve into the one or more acquired depictions showing the structure of interest, and placing each of the one or more imported model(s) at respective positions within the structure of interest shown in the depiction(s). For purposes of this disclosure, and as will be described more fully below, a "position" within the structure of interest shown in the acquired depiction(s) is intended to connote an axial position relative to an axis that, in at least some embodiments, is perpendicular to the mitral plane, and/or an orientation relative to an axis that is, in at least some embodiments, perpendicular to the mitral plane.

Figure 10B:
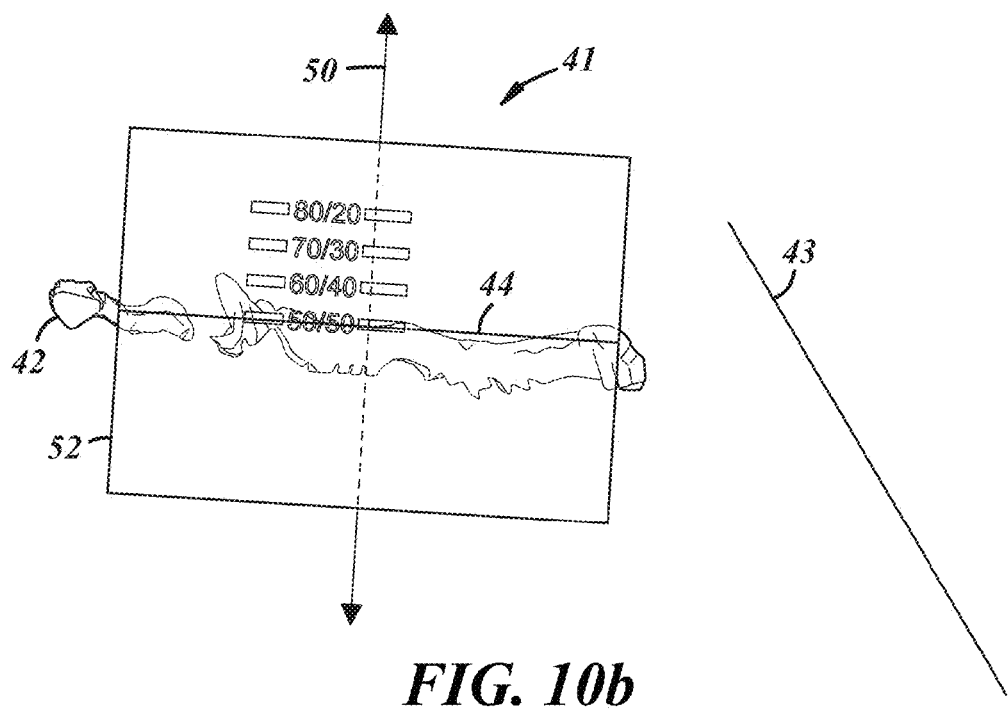

To better illustrate, FIG. 10*b* depicts the model 41 that includes or shows the model 42 of a previously-implanted mitral ring, and an axis 50 that in this example extends perpendicular to the representation of the mitral plane 44. A computer-generated valve model 52 is imported into the model 41 and placed at a particular axial position within the mitral ring model 42, which, in this particular illustration, is the "50/50" valve position meaning that approximately 50% of the valve model is disposed on either side of the mitral ring model 42, and thus, approximately 50% of the valve would extend into each of the left atrium and left ventricle.

Figure 11B:
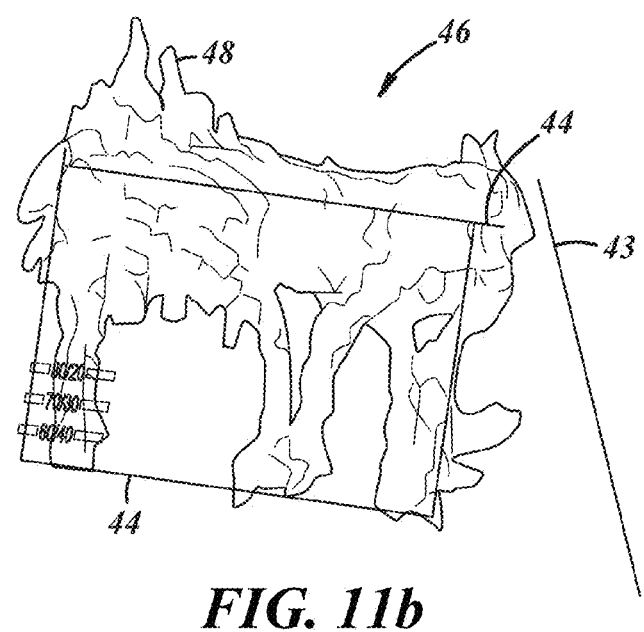

Similarly, in FIG. 11*b* depicts the model 46 that includes or shows the model 48 of a previously-implanted prosthetic mitral valve, and an axis 54 that in this example extends perpendicular to a representation of the mitral plane 44. A computer-generated valve model 56 is imported into the model 46 and placed at a particular axial position within the model 48 of the previously-implanted prosthetic valve. In this illustration, the mitral plane 44 is offset to the bottom of the model 48 and defines a 0% position meaning that no part of the valve model extends beyond the boundary of the model 48. The valve model 56 is then aligned with the offset mitral plane 44 such that it assumes the 0% position.

In any event, the placement of the valve model imported in step 108 may be controlled entirely by the software program using a plane-to-plane align tool/operation wherein the mitral plane is used as the fixed entity and a portion of the valve model is used as the moving entity. It will be appreciated, however, that other ways of placing the valve model may certainly be used instead, including manually by a user using the user interface device(s) 26 of the system 20.

In an embodiment, following the importation of a valve model in step 108, method 100 may proceed to one or more subsequent steps, such as, for example, step 110 described below. In such an embodiment, step 108, and in some embodiments, steps 106 and 108 may thereafter be repeated to evaluate a different position within the model of the structure of interest. Alternatively, in other embodiments, step 108 may be repeated any number of times to import one or more additional valve models into the model of the structure of interest wherein each valve model is placed at a different position prior to method 100 moving to a subsequent step.

Figure 10C:
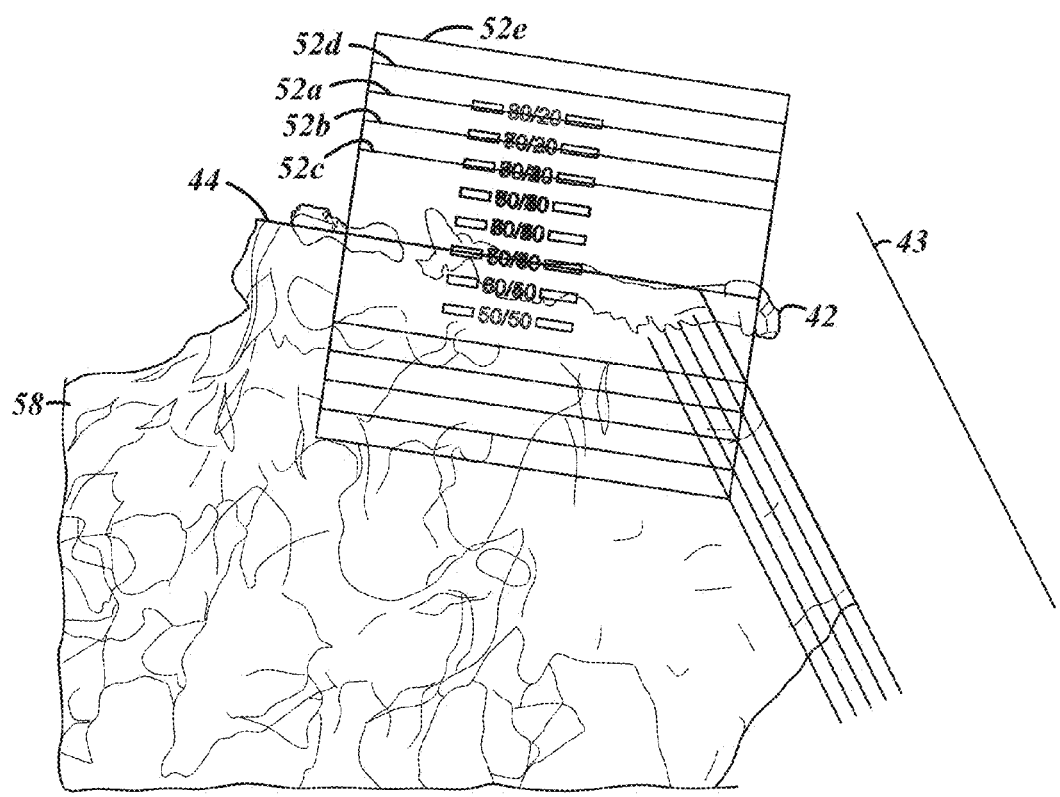

By way of illustration, FIG. 10*c* depicts an embodiment wherein step 108 was performed five (5) times to import five (5) different valve models 52 (i.e., valve models 52*a*-52*e*) into the model 42 of the structure of interest (i.e., model of a previously-implanted mitral ring). FIG. 10*c* also shows or includes a model 58 of a portion of the LVOT blood pool volume. As shown, each valve model 52 is disposed at a different axial position relative to the axis 50. For example, a first valve model 52a may be disposed at the 50/50 position described above with respect to FIG. 10b; a second valve 52b model may be disposed at a position whereat the valve extends 10% further into the left ventricle from the 50/50 position (i.e., the "60/40" position); a third valve model 52c may be disposed at a position whereat the valve extends 20% further into the ventricle from the 50/50 position (i.e., the "70/30" position); a fourth valve model 52d may be disposed at a position whereat the valve extends 10% further into the left atrium from the 50/50 position (i.e., the "40/60" position); and a fifth valve model 52e may be disposed at a portion whereat the valve extends 20% further into the atrium from the 50/50 position (i.e., the "30/70" position). As can be seen in FIG. 10c, in an embodiment, the valve models 52 may be placed in their corresponding positions using markers or indicators on the valve models 52. For example, each valve model 52 may have markers or indicators corresponding to the 50/50, 60/40, 70/30, etc. positions. When it is desired to place a valve model at a particular position, the corresponding marker on the valve model is aligned with the representation 44 of the mitral plane.

Figure 11C:
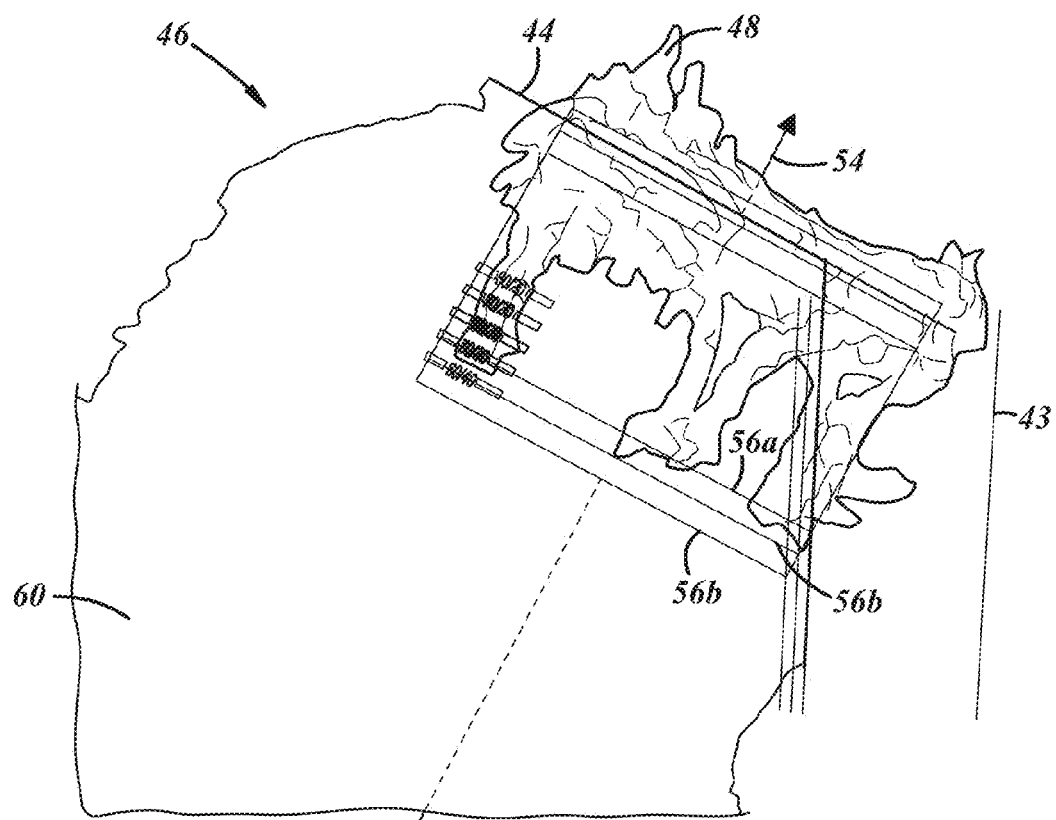

FIG. 11c depicts an embodiment wherein step 108 was performed three (3) times to import three (3) different valve models 56 (i.e., valve models 56a-56c) into the model 48 of the structure of interest (i.e., model of a previously-implanted prosthetic valve). FIG. 11c also shows or includes a model 60 of a portion of the LVOT blood pool volume. As shown, each valve model 56 is disposed at a different axial position relative to the axis 54. For example, a first valve model 56a may be disposed at the 0% position described above with respect to FIG. 11b; a second valve model 56b may be disposed at a position whereat the valve extends 10% further into the left ventricle from the 0% position; and a third valve model 56c may be disposed at a position whereat the valve extends 20% further into the ventricle from the 0% position (i.e., 10% further than the 10% position). As discussed above with respect to FIG. 10c, the valve models 56 may be placed in their corresponding positions using markers or indicators on the valve models 52. When it is desired to place a valve model at a particular position, the corresponding marker on the valve model is aligned with the representation 44 of the mitral plane that was offset to the bottom of the model 48.

Accordingly, it will be appreciated that any number of valve models may be imported in step 108, and that those valve models may be placed any number of different axial positions within the model of the structure of interest, including, but certainly not limited to, those described above. In any event, in an embodiment wherein step 108 is repeated one or more times before method 100 proceeds to a subsequent step, method 100 would proceed to a subsequent step only once the desired number of valve models have been imported and placed in the model of the structure of interest.

While the description of step 108 has thus far been with respect designating one or more hypothetical valve positions in terms of axial position(s) of one or more valve models within the depiction of the structure of interest, step 108 may additionally or alternatively comprise designating one or more positions in terms of the angular orientation of one or more valve models within the depiction of the structure of interest. More particularly, whereas each of the valve models 52 (i.e., 52a-52f) in FIG. 10c and the valve models 56 (i.e., 56a-56c) in FIG. 11c are coaxially arranged relative to the respective axes 50, 54, in other embodiments, step 108 may comprise placing one or more valve models in such way that the valve model(s) are not all coaxially arranged, but rather one or more of the valve models may have a different angular orientation than one or more of the other valve models. In such an embodiment, the valve models may be placed at the same axial position or at one or more different axial positions, depending on the implementation.

Figure 12A:
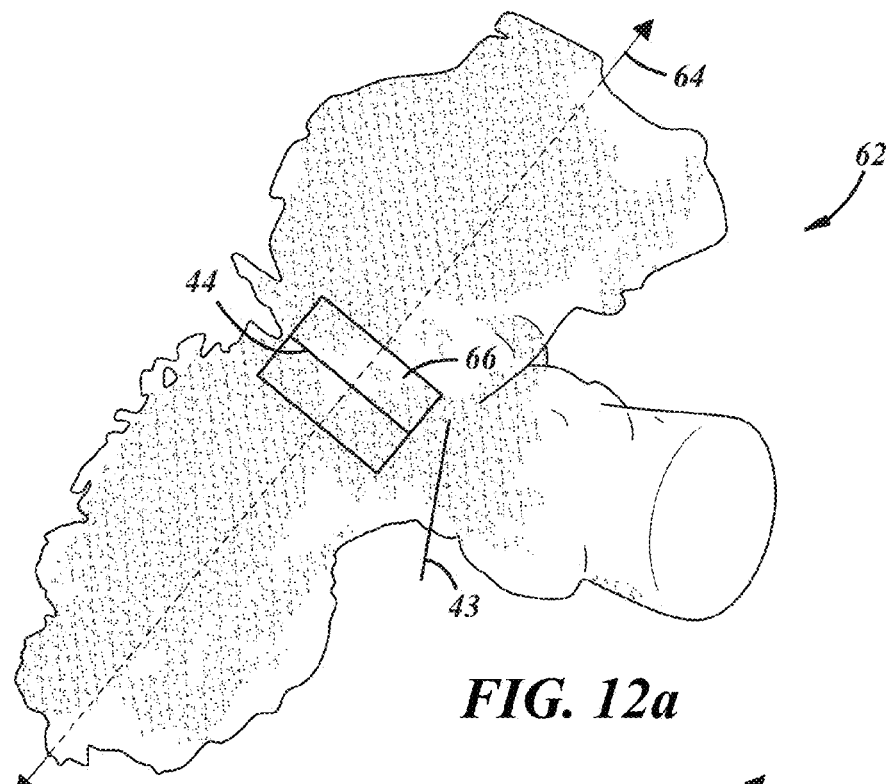
FIGS. 12a-12d are depictions of models that may be used in the performance of the method illustrated in FIG. 4, and showing an illustrative embodiment of how the method illustrated in FIG. 4 is carried out.
Figure 12B:
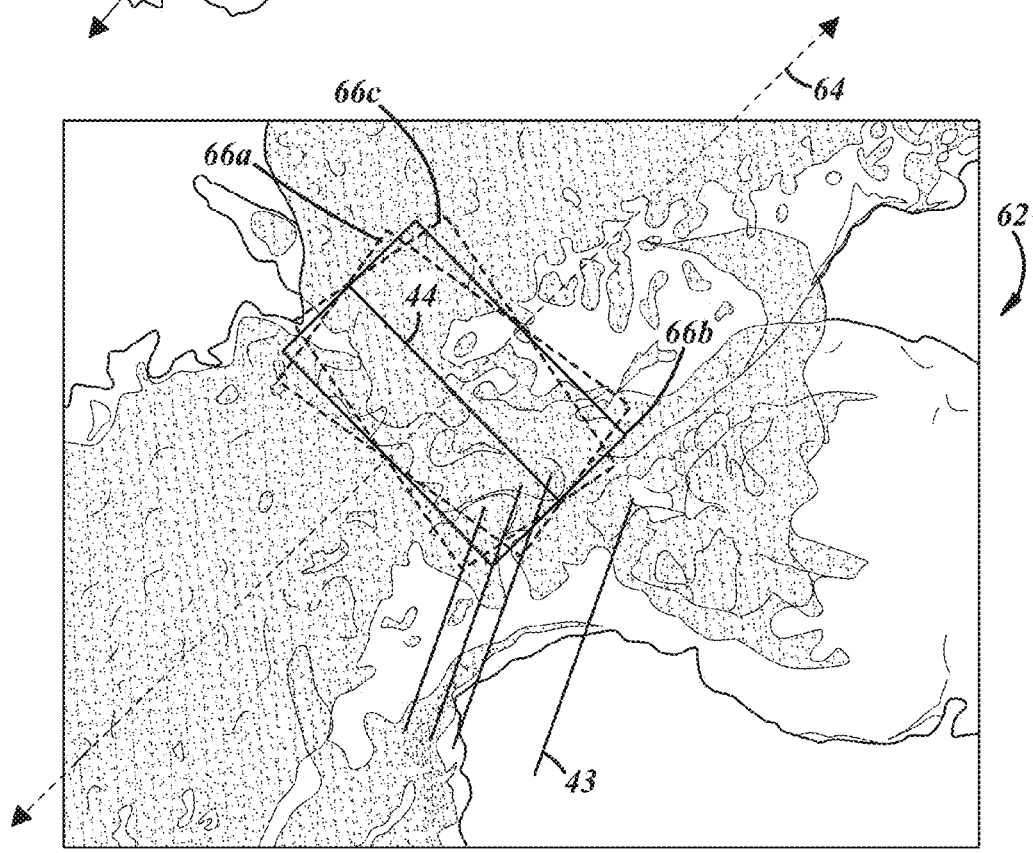

To better illustrate, reference is made to FIGS. 12a and 12b. FIG. 12a depicts a model 62 of a structure of interest and an axis 64 that in this example extends perpendicular to a representation 44 of the mitral plane. A computer-generated valve model 66 is imported into the model 62 and placed at a particular axial position therein. FIG. 12b depicts an embodiment wherein step 108 was performed three (3) times to import three (3) different valve models 66 (i.e., valve models 66a-66c) into the model 62 of the structure of interest. As illustrated in FIG. 12b, each valve model 66 is disposed at a different angle relative to the axis 64 and each other. For example, a first valve model 66a may be disposed at approximately a zero degree angle relative to the axis 64; a second valve model 66b may be disposed at a first non-zero angle relative to the axis 64; and a third valve model 66c may be disposed at a second non-zero angle relative to the axis 64 that is different than the first non-zero angle.

Accordingly, it will be appreciated that the designation in step 108 of one or more "positions" in one or more depictions acquired in step 106 may take any number of forms, and therefore, the present disclosure is not intended be limited any particular form(s). Additionally, in an embodiment, step 108 may be performed automatically by, for example, the ECU 22 of system 20. In other embodiments, however, step 108 may be at least partially performed manually by a user. For example, the model acquired in step 106 may be displayed on the display device 24 of system 20 and a user may use the user interface device(s) 26 to command the importation of a valve model and to move the valve model into a desired position. Accordingly, the present disclosure is not intended to be limited to any particular way(s) of performing step 108.

Following step 108, method 100 may progress to a step 110 of predicting, for each of the positions designated in step 108 (e.g., axial positions, angular orientations, or both), an amount of blood flow obstruction through the LVOT of the patient's heart that would occur if the prosthetic valve was actually placed at a corresponding position in the actual structure of interest. For purposes of this disclosure, the term "corresponding," as it relates to a corresponding position in the actual structure of interest, is intended to include instances where the position in the actual structure of interest is exactly the same as the designated position in the depiction(s), or and instances where the positions are not exactly the same but are nonetheless within a particular tolerance (e.g., distance, angle, etc.) deemed suitable or acceptable by those of ordinary skill in the art for accurately performing the methodologies described herein. As will be described more fully below, for a given valve position designated in step 108, step 110 may comprise determining a cross-sectional surface area of the blood pool volume of the LVOT corresponding to that designated position, and predicting the blood flow obstruction through the LVOT based at least in part on that determined cross-sectional surface area.

In an embodiment, such as that described above wherein step 106 comprises acquiring a 3D model showing the structure of interest and the LVOT blood pool volume, and step 108 comprises importing one or more valve models into that model of the structure of interest, step 110 comprises predicting, for each of the valve model positions (e.g., axial positions, angular orientations, or both), an amount of blood flow obstruction through the LVOT of the patient's heart that would occur when the prosthetic valve is actually placed at a corresponding position in the actual structure of interest. In one illustrative embodiment, the performance of step 110 for a given valve model position may comprise a number of substeps.

More particularly, in a substep 112, a representation of the aortic plane may be offset to a point in the acquired model at which the corresponding valve model intersects the blood pool volume. In an embodiment, this point comprises the furthest point into the blood pool volume model that the valve model reaches. By way of illustration, FIG. 10c illustrates an embodiment wherein the structure of interest is a previously-implanted mitral ring, and five valve models 52 have been imported into the model 42 of the mitral ring. For each position of the five valve models, a representation of the aortic plane 43 is offset to a point at which the corresponding valve model 52 intersects the blood pool volume model 58. As seen in FIG. 10c, the intersection point in this particular example for a given valve model is the bottom edge of the valve model closest to the original representation of the aortic plane 43, and thus the aortic annulus. FIG. 11c similarly illustrates substep 112 for an embodiment wherein the structure of interest is a previously-implanted prosthetic valve represented by reference numeral 48; and FIG. 12b also similarly illustrates substep 112 for an embodiment wherein imported valve models 66 are arranged at different angles.

Once a representation of the aortic plane is offset as described above for the given valve model position being evaluated, a substep 114 of step 110 comprises sectioning or cutting the acquired model, and the blood pool volume shown therein, in particular, along the offset aortic plane. The cross-sectional surface area of the blood pool volume along the offset representation (i.e., the "cut line") is then determined in a substep 116. In an embodiment, one or both of substeps 114, 116 may be performed automatically by, for example, the ECU 22 of system 20. In other embodiments, however, one or both of the substeps may be at least partially performed manually by a user. For example, once the model is sectioned or cut in substep 114, substep 116 may comprise rotating the cut volume so that the cross-sectional surface or cut surface can be seen on, for example, the display device 24 of the system 20, and may then comprise manually selecting the surface for which the surface area is to be determined using, for example, the user interface device(s) 26 of the system 20. The surface area may then be automatically determined (e.g., calculated) by the ECU 22 of the system 20.

Figure 10D:
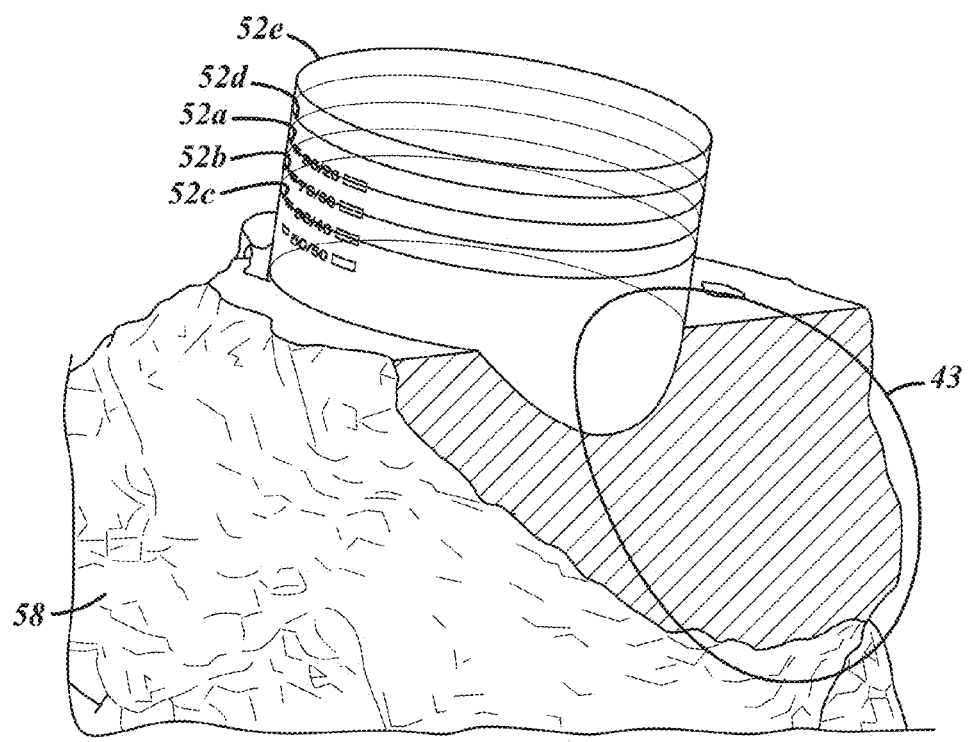
Figure 11D:
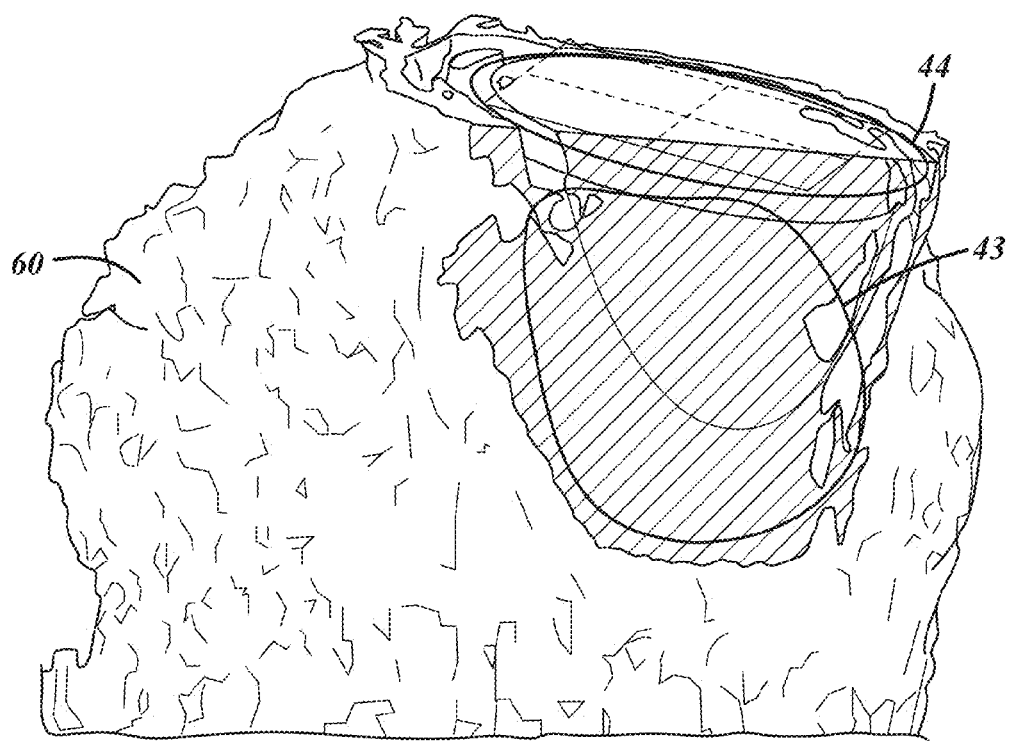
Figure 12C:
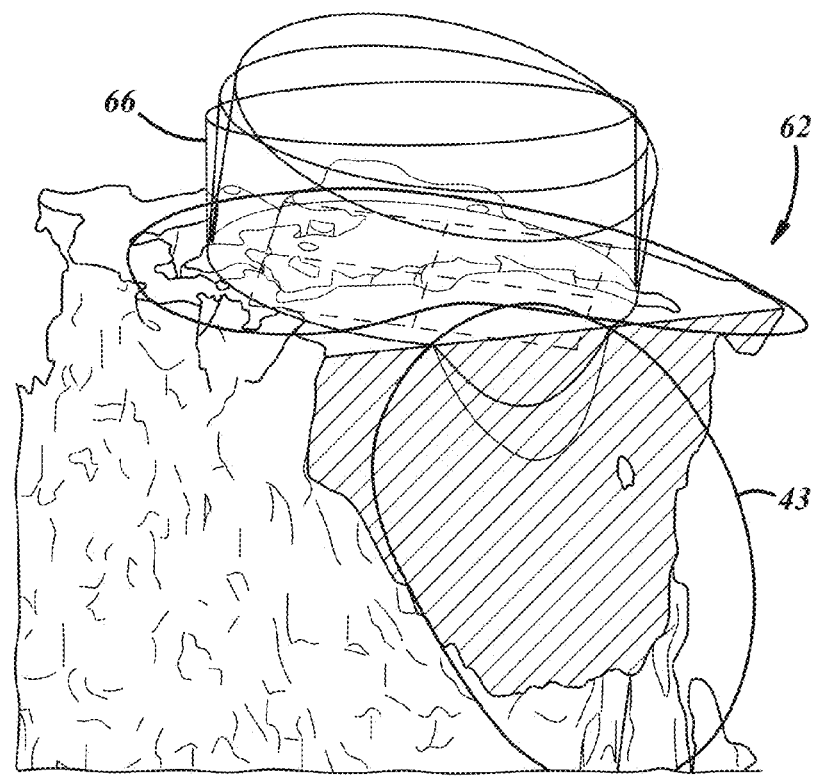

In any event, it will be appreciated that the cross-sectional surface along the cut line for which the surface area is to be determined will include both the cross-sectional surface of the blood pool volume and a portion of the surface of the valve model disposed between the mitral plane and the LVOT. Accordingly, in an embodiment, step 110 may further include a substep (not shown) that may be performed prior to substep 116 and that includes sectioning or cutting the acquired model along the mitral plane. In any event, the surface area determined in substep 116 is considered to be the "unobstructed" surface area of the LVOT blood pool volume or the surface area "without a prosthetic valve," and will be referred to below as the "first surface area." As will be described below, the obstruction of the blood flow through the LVOT caused by the prosthetic valve being placed in a corresponding position within the structure of interest can be predicted based at least in part on this first, unobstructed surface area. Each of FIGS. 10d, 11d, and 12c illustrate examples of the performance of substeps 114, 116 of step 110, with FIG. 10d illustrating an embodiment wherein the structure of interest is a previously-implanted mitral valve, FIG. 11d is embodiment wherein the structure of interest is a previously-implanted prosthetic heart valve, and FIG. 12c is an embodiment wherein the valve models imported into the model acquired in step 106 are arranged at different angles.

Figure 10E:
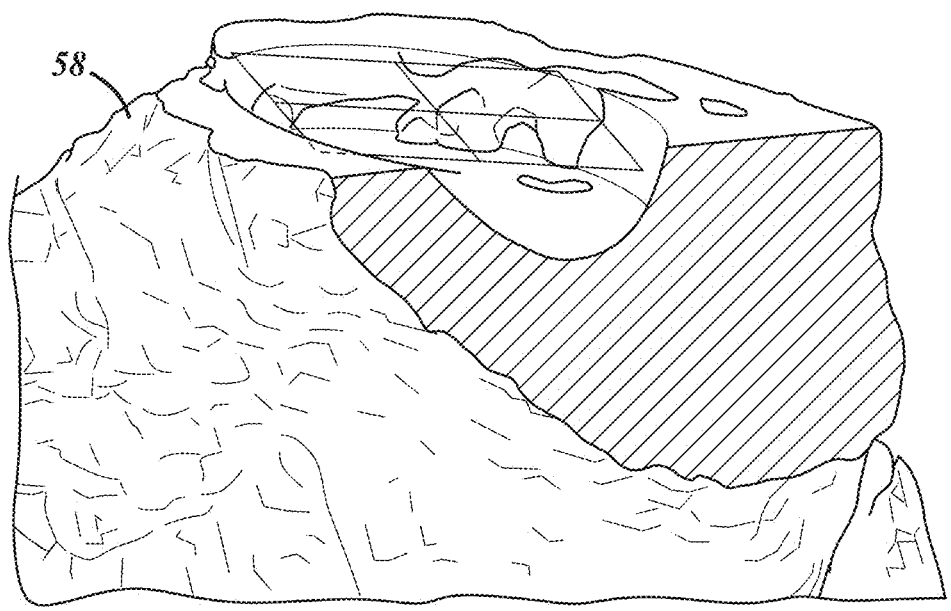
Figure 11E:
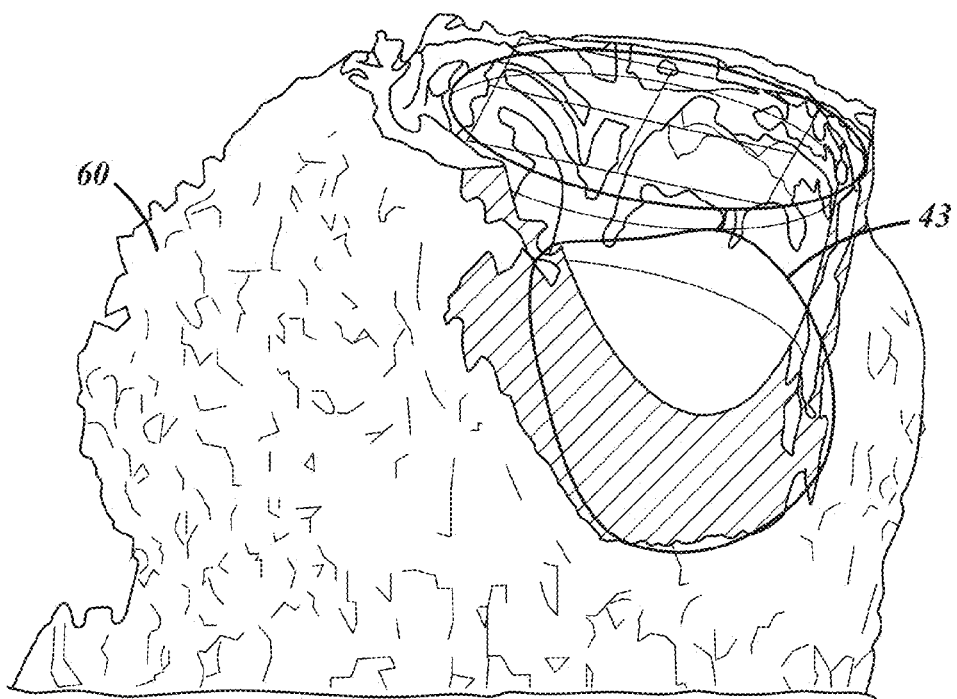
Figure 12D:
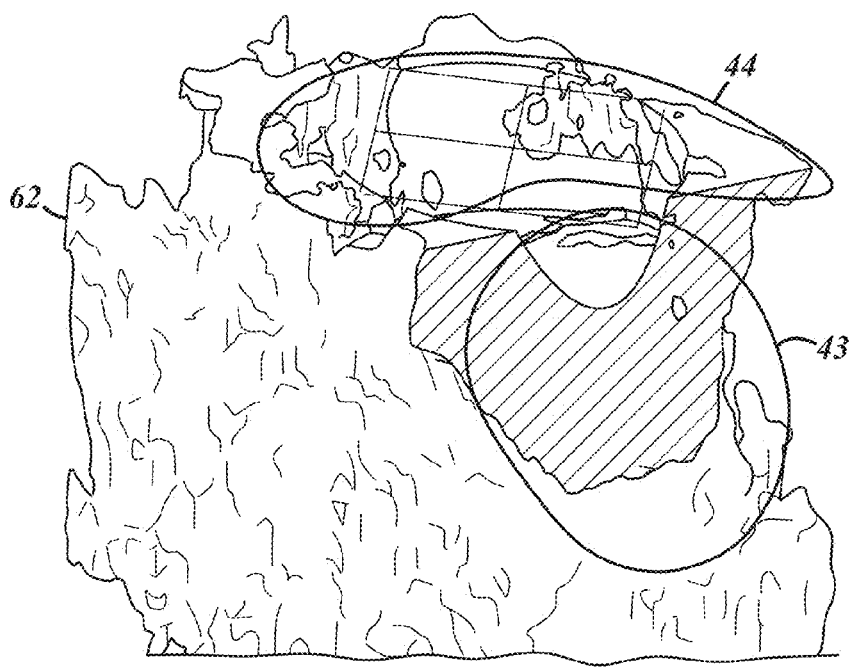

Following the determination of the first, unobstructed surface area in substep 116, step 110 may comprise a further substep 118 of removing the one or more valve models that were previously-imported into the acquired model using, for example, Boolean subtraction, and then determining in a substep 120 a second cross-sectional surface area of the surface along the cut line. Because the valve model(s) were removed from the acquired model, the surface along the cut line will include only the cross-sectional surface of the blood pool volume, and the surface area of this surface is considered to be the "obstructed" surface area or the surface area "with a prosthetic valve." Each of FIGS. 10e, 11e, and 12d illustrate examples of the performance of substeps 118,120 of step 110, with FIG. 10e illustrating an embodiment wherein the structure of interest is a previously-implanted mitral valve, FIG. 11e is embodiment wherein the structure of interest is a previously-implanted prosthetic heart valve, and FIG. 12d is an embodiment wherein the valve models imported into the model acquired in step 106 are arranged at different angles.

In an embodiment, one or both of substeps 118, 120 may be performed automatically by, for example, the ECU 22 of system 20. In other embodiments, however, substeps 118, 120 may be at least partially performed manually by a user. For example, as it relates to substep 118, the model may be displayed on the display device 24 of system 20 and a user may use the user interface device(s) 26 to select the portions of the model to be removed (e.g., the valve models), and to then command that that or those portions be removed. As it relates to substep 120, a user may manually select the surface for which the surface area is to be determined using, for example, the user interface device(s) 26 of the system 20. The surface area may then be automatically determined (e.g., calculated) by the ECU 22 of the system 20. Accordingly, the present disclosure is not intended to be limited to any particular way of performing substeps 118, 120.

In any event, the obstruction of the blood flow through the LVOT caused by the prosthetic valve being placed in a corresponding position within the structure of interest can be predicted based at least in part on the second determined surface area. In an embodiment, however, the obstruction can be predicted based on both the first and second determined surface areas by subtracting the second surface area (i.e., surface area "with prosthetic valve") from the first surface area (i.e., surface area "without prosthetic valve"), and dividing the result by the first surface area. The result is a percentage representing the amount of the LVOT that would be obstructed, and thus, the amount of blood flow obstruction through the LVOT that would be caused for a given valve position.

In an embodiment, prior to removing the valve model(s) in substep 118, step 110 may comprise a substep of duplicating or copying the model having the valve model(s) disposed therein to create a second model, and then performing substeps 118, 120 using the second model. Both of the models may then be saved for future use such that models showing the first and second cross-sectional areas are maintained.

In an instance wherein multiple valve models have been imported into the model acquired in step 106, and thus, multiple positions are being evaluated, the step 110 may be performed for each valve position one-at-a-time such that the obstruction prediction is performed one valve position at a time. In such an instance, separate models may be used for each iteration of step 110. Alternatively, each substep of step 110 may be performed for each valve position before moving on to the next substep such that step 110 as a whole is performed only once. In such an instance, separate models may be used for each valve position being evaluated.

In any event, once each of the one or more positions designated in step 108, or at least a certain number of that or those positions, have been evaluated, and an obstruction prediction for each relevant position has been made in step 110, method 100 may proceed to a step 122 of determining a position or location in the structure of interest at which to actually place the prosthetic device based at least in part of the predicted blood flow obstruction(s).

In an embodiment, once steps 102-122 have been performed for one of the diastolic and systolic phases of the cardiac cycle, method 100 may be repeated for other of the diastolic and systolic phases, and the predictions from step 110 and/or determinations from step 122 may be used together to determine an optimal position (i.e., axial position and/or orientation) to place a prosthetic for that particular patient.

In addition to the above, knowing the cross-sectional surface area of the blood pool volume of the LVOT (i.e., the second, obstructed surface area discussed above) when a prosthetic valve is at a particular location or position within a structure of interest may also allow for the determination or evaluation of other parameters of interest. For example, if a patient's stroke volume information is also available, the increase in peak velocity (cm/sec) that the LVOT will experience with the prosthetic valve in place can be determined by dividing the stoke volume (ml/sec) by the LVOT area ($mm^2$).

Figure 13:
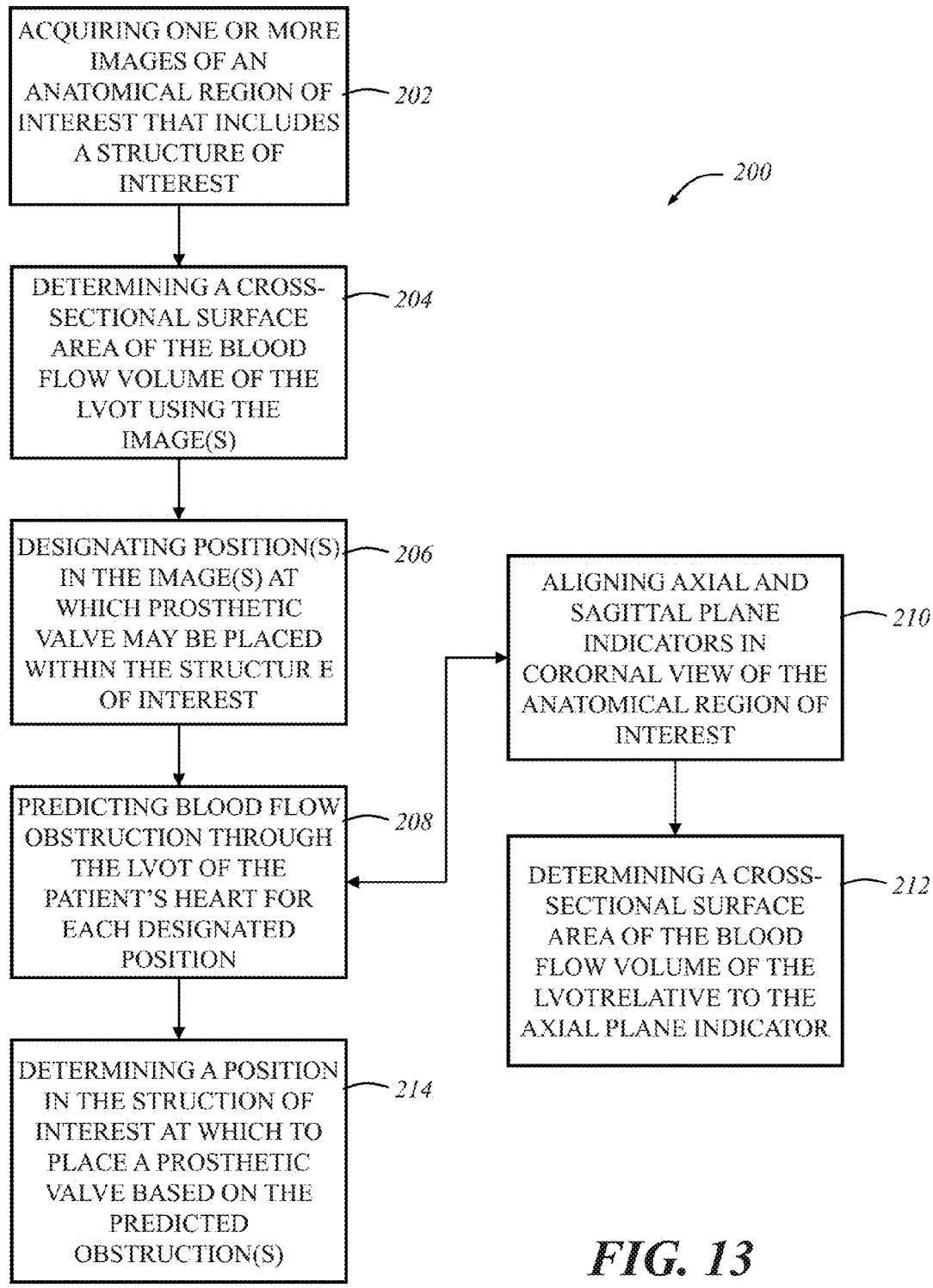
FIG. 13 is a flowchart of another illustrative embodiment of a method that may be used to evaluate prosthetic heart valve placement.

With reference to FIG. 13, another illustrative embodiment of a method (method 200) for evaluating the placement of an implantable prosthetic device within a structure of interest located an anatomical region of a patient's body is shown. As with the embodiment described above (i.e., method 100), the prosthetic device may be, for example, a prosthetic heart valve, and in an embodiment, a prosthetic mitral heart valve; and thus, in an embodiment, the anatomical region in which the structure of interest is located may at least partially include the patient's heart (or at least a portion thereof, for example, one or more of the left atrium, left ventricle, aorta, and LVOT of the patient's heart). For purposes of illustration, the description below will be primarily with respect to evaluating the placement of a prosthetic mitral heart valve. It will be appreciated, however, that the methodology described herein may be used to evaluate the placement of other prosthetic devices.

In at least some embodiments, all of the steps of method 200 may be performed or carried out by an appropriately or suitably configured system, for example and without limitation, the system 20 described above, either alone or in conjunction with input from a user (e.g., physician). In other embodiments, however, some of the steps may be performed or carried out by different systems such that certain steps may be performed by one system (e.g., system 20), and other steps may be performed by one or more other suitable systems. For purposes of illustration, the description below will be primarily with respect to an embodiment wherein the method 200 is performed by the system 20 described above either alone or in conjunction with user input. It will be appreciated, however, that the present disclosure is not limited to such an embodiment. Additionally, it will be appreciated that unless otherwise noted, the performance of method 200 is not meant to be limited to any one particular order or sequence of steps, or to any particular component(s) for performing the steps.

In an embodiment, method 200 comprises a step 202 of acquiring one or more depictions of an anatomical region of interest of the patient's body that includes the structure of interest, and wherein each of the one or more depictions shows the structure of interest, the blood pool volume of the LVOT of the patient's heart, or both. In an embodiment, the one or more depictions comprise one or more images each showing at least a portion of the anatomical region of interest. These images may be obtained from a memory device, for example, the memory device 30 of the system 20. Alternatively, the images may be acquired by generating them from image data, for example and without limitation, CT image data. While CT image data is specifically identified herein, it is contemplated that image data corresponding to imaging modalities other than CT, such as, for example, one or more of those modalities identified elsewhere above, may be used in addition to or instead of CT image data.

Figures 14A, 14B:
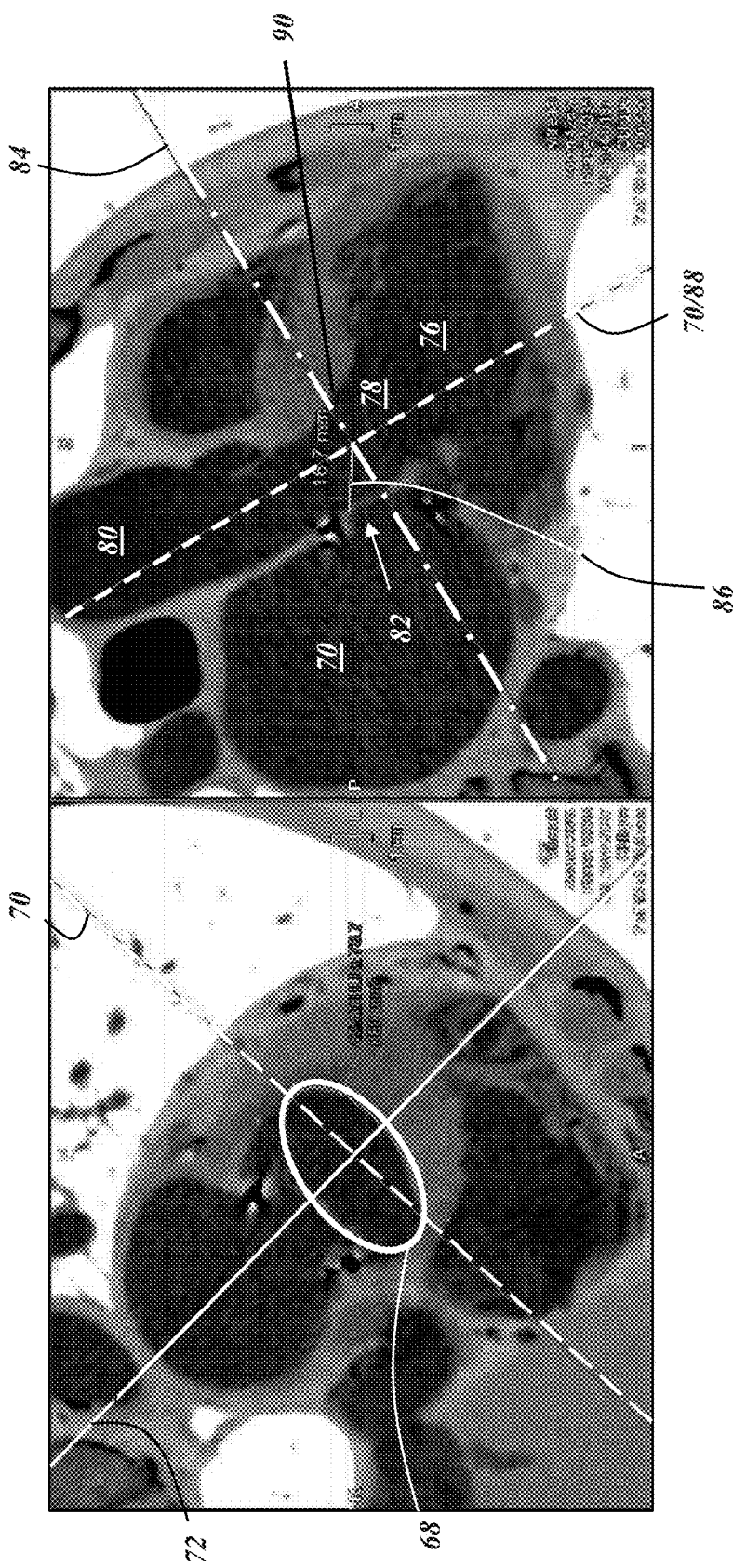
FIGS. 14a-14c are images that may be used in the performance of the method illustrated in FIG. 13, and showing an illustrative embodiment of how the method illustrated in FIG. 13 is carried out.

In any event, in an embodiment, step 202 may comprise obtaining a three-dimensional digital imaging and communications in medicine (dicom) dataset corresponding to the anatomical region of interest. This dataset may be processed using a multi-planar reformatting (MPR) technique to generate or obtain a set of 2D images or views along the sagittal, coronal and axial planes, and these images or views may then be used as described below. For example, FIG. 14a depicts an acquired image of the anatomic region of interest taken along the sagittal plane and showing, among other things, the cross-sectional surface area of the blood pool volume of the LVOT, represented by reference numeral 68 in FIG. 14a. Plane indicators 70, 72 representing the axial and coronal planes, respectively, are also shown in FIG. 14a. FIG. 14b depicts an acquired image of the same anatomical region of interest shown in FIG. 14a taken along the coronal plane and showing, among other structures, the left atrium 74, the left ventricle 76, the LVOT 78, the aorta 80, and the structure of interest 82, which, in this instance, is the patient's native mitral valve. Plane indicators 70, 84 representing the axial and sagittal planes are also shown. In this particular embodiment, inverted maximal intensity projection imaging is used to generate the images in FIGS. 14a and 14b so as to render the blood pool volume in each cardiac structure dark and the surrounding tissue light to better delineate the clear intersections of the blood pool volume of, for example, the LVOT. In any event, image data and images corresponding thereto may be acquired for both the diastolic and systolic phases of the patient's cardiac cycle.

Once the depictions (i.e., images) are acquired in step 202, method 200 may proceed to a step 204 of determining an unobstructed cross-sectional surface area of the blood pool volume of the LVOT. This surface area is considered to be unobstructed because no prosthetic valve models or representations have been imported into, or hypothetical valve positions designated in, the acquired image(s), and as such, the LVOT is effectively "unobstructed" by a prosthetic valve model. In an embodiment, a sagittal view of the anatomical region of interest showing the cross-section of the LVOT blood pool volume may be used to determine this unobstructed cross-sectional surface area. Step 204 may be performed automatically by, for example, the ECU 22 of the system 20. Alternatively, step 204 may be performed by the ECU 22 in conjunction with one or more user inputs made through the user interface device(s) 26 of the system 20. For example, an image such as that shown in FIG. 14*a* may be displayed on the display device 24 of the system 20 and a user may use the user interface device(s) 26 to outline or select the portion of the image corresponding to the cross-section of the LVOT blood pool volume (represented by reference numeral 68 In FIG. 14*a*). Accordingly, it will be appreciated that the first cross-sectional surface area of the LVOT blood pool volume may be determined in a number of ways, and as such, the present disclosure is not intended to be limited to any particular way(s) of doing so. In any event, as will be described in greater detail below, this first cross-sectional surface area may be used in a subsequent step of method 200.

Following step 202 and, in at least some embodiments, step 202 and step 204, method 200 may comprise a step 206 of designating one or more positions in at least one of the acquired depictions (e.g., images) showing the structure of interest, wherein each designated position corresponds to a respective position or location in the structure of interest at which the prosthetic valve may be placed. In an embodiment, step 206 may comprise importing one or more models or other representations of the prosthetic valve into the at least one of the acquired images, and placing each of the one or more imported model(s) at respective positions within the structure of interest shown in the image(s). In another embodiment, step 206 may comprise a user manually drawing or tracing a position that a portion of prosthetic valve may assume within the structure of interest on one or more of the acquired images. For example, FIG. 14*b* illustrates a designation or representation 86 representing a portion of the frame of a prosthetic valve, wherein the designation 86 is inserted into area of the image corresponding to the mitral annulus of patient's heart, and extending into the LVOT. In any event, it will be appreciated that the present disclosure is not intended to be limited to any particular way of designating position(s) in the acquired image(s), but rather any suitable way may be used.

Following step 206, method 200 may proceed to step 208 of predicting, for each of the one or more designated positions, an amount of blood flow obstruction through the LVOT of the patient's heart that would occur if the prosthetic valve was to be placed at a position in the structure of interest that corresponds to the position designated in the at least one of the one or more acquired images. In an embodiment, step 208 may comprise a number of substeps.

For example, in an illustrative embodiment, step 208 may comprise a substep 210 of aligning both the axial and sagittal plane indicators in the image taken along the coronal plane with a point at which a portion of the designated position of the prosthetic valve intersects the LVOT blood pool volume. In an embodiment, this point may correspond to the furthest point into the blood pool volume that the valve model designation reaches. For example, as shown in FIG. 14*b*, the axial plane indicator 70 and the sagittal plane indicator 84 are both aligned with the end of the valve position designation 86 that is the furthest away from the mitral annulus, and disposed the furthest into the LVOT. In an embodiment, once the axial and sagittal plane indicators are aligned, substep 210 may further comprise angling the intersection of the plane indictors such that the axial plane indicator 70 is parallel to a longitudinal axis 88 of the LVOT extending between the left ventricle and the aorta, and the sagittal plane indicator 84 is perpendicular to the opposite basal anteroseptal wall 90 of the left ventricle. An illustration of this is shown in FIG. 14*b*. Thereafter, in an embodiment, the intersection, and therefore the plane indicators, may be angulated to obtain the smallest LVOT surface area. The amount by which the plane indicators are angulated will be patient specific and will be based on, for example, the angulation of the patient's anteroseptal wall. For purposes of this disclosure, the term "parallel" in the context of orienting the axial plane indicator with the longitudinal axis of the LVOT is intended to include instances where the plane indicator is exactly parallel with the longitudinal axis, as well as instances where the plane indicator is not exactly parallel but is nonetheless within a particular tolerance deemed suitable or acceptable by those of ordinary skill in the art for accurately performing the methodologies described herein (e.g., 0-10 degrees relative to the axis). Similarly, for purposes of this disclosure, the term "perpendicular" in the context of orienting the sagittal plane indicator with the opposite basal anteroseptal wall is intended to include instances where the plane indicator is exactly perpendicular with the anteroseptal wall, as well as instances where the plane indicator is not exactly perpendicular but is nonetheless within a particular tolerance deemed suitable or acceptable by those of ordinary skill in the art for accurately performing the methodologies described herein. (e.g., 0-10 degrees relative to a plane that is exactly perpendicular to the anteroseptal wall).

In an embodiment, substep 210 may be performed automatically by the ECU 22 of the system 20; while in other embodiments, it may be performed by the ECU 22 in conjunction with input provided by the user using, for example, the user interface device(s) 26. Accordingly, the present disclosure is not intended to be limited any particular way(s) of performing substep 210.

Following the alignment of the plane indicators with the position designation in substep 210, step 208 may comprise a further substep 212 of determining a cross-sectional surface area of the blood pool volume of the LVOT that remains or is preserved following the designation of one or more valve positions in step 208. In other words, substep 212 comprises determining an "obstructed" cross-sectional surface area of the LVOT blood pool volume. In an embodiment, an image of the anatomical region of interest taken along the sagittal plane and showing the cross-section of the LVOT blood pool volume along with an axial plane indicator oriented consistent with the position and orientation of the axial plane indicator that was aligned in the image taken along the coronal plane in substep 210 may be used to determine the obstructed surface area.

Figure 14C:
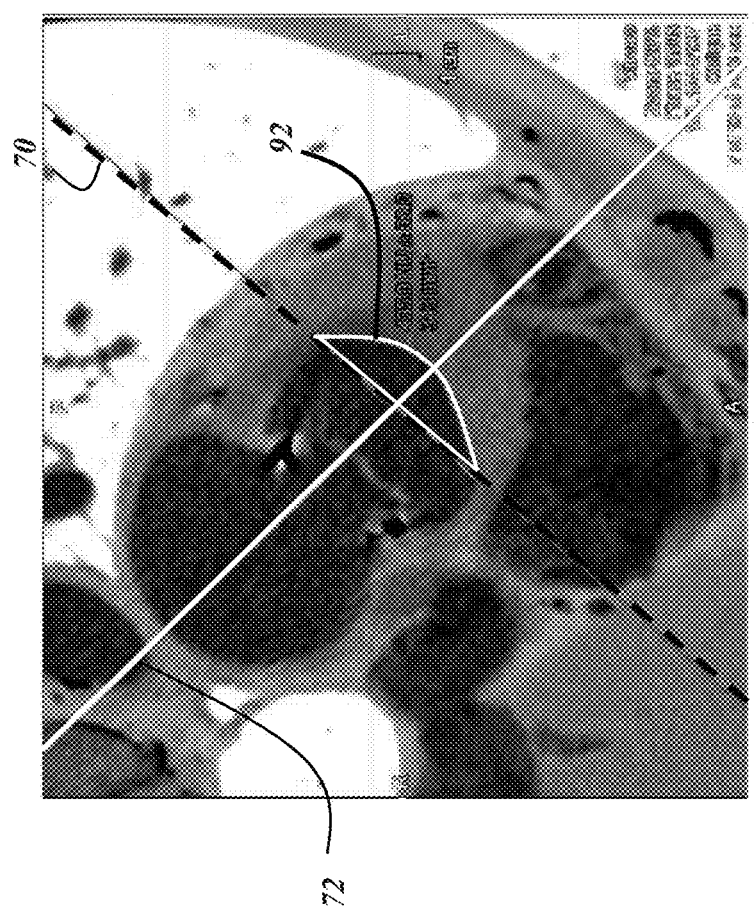

For example, FIG. 14*c* depicts an image of the anatomic region of interest taken along the sagittal plane and showing, among other things, the cross-sectional surface area of the blood pool volume of the LVOT, and having the axial plane indicator 70 oriented consistent with the position and orientation of the axial plane indicator 70 in FIG. 14*b*. In such an embodiment, the preserved or unobstructed cross-sectional area of the LVOT blood pool volume may be determined by calculating the surface area of the portion of the cross-sectional surface of the LVOT blood pool volume that is between the axial plane indicator 70, which is representative of a designated position of a prosthetic valve, and the basal anteroseptal. The area of interest is represented by reference numeral 92 in FIG. 14*c*. As with one or more of the steps described above, substep 212 may be performed automatically by, for example, the ECU 22 of the system 20. Alternatively, substep 212 may be performed by the ECU 22 in conjunction with one or more user inputs made through the user interface device(s) 26 of the system 20. For example, an image such as that shown in FIG. 14c may be displayed on the display device 24 of the system 20 and a user may use the user interface device(s) 26 to outline or select the portion of the image corresponding to the preserved cross-sectional surface area of the LVOT blood pool volume (represented by reference numeral 92 in FIG. 14c). Accordingly, it will be appreciated that the preserved or obstructed cross-sectional surface area of the LVOT blood pool volume may be determined in a number of ways, and as such, the present disclosure is not intended to be limited to any particular way(s) of doing so.

Once the obstructed cross-sectional surface area is determined in substep 212, the obstruction of the blood flow through the LVOT caused by a prosthetic valve being placed in a corresponding position within the structure of interest can be predicted based at least in part on the obstructed cross-sectional surface area. In an embodiment, however, the obstruction is predicted based on both unobstructed cross-sectional surface area determined in step 204 and the preserved or obstructed cross-sectional surface area determined in substep 212 of step 208. More particularly, in an embodiment, the obstructed surface area may be subtracted from the unobstructed surface area, and the result may be divided by the unobstructed surface area. The result is a percentage representing the amount of the LVOT that would be obstructed, and thus, the amount of blood flow obstruction through the LVOT that would be caused for a given valve position.

In any event, once an obstruction prediction for each relevant valve position has been made in step 208, method 100 may proceed to a step 214 of determining a position or location in the structure of interest at which to actually place the prosthetic device based at least in part of the predicted blood flow obstruction(s).

In an embodiment, once steps 202-214 have been performed for one of the diastolic and systolic phases of the cardiac cycle, method 200 may be repeated for other of the diastolic and systolic phases, and the predictions from step 208 and/or determinations from step 214 may be used together to determine an optimal position (i.e., axial position and/or orientation) to place a prosthetic for that particular patient.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A computer-implemented method for evaluating the placement of a prosthetic device in a patient's body, comprising:
   acquiring one or more depictions of an anatomical region of interest of the patient's body that includes a first anatomical structure of interest in which the prosthetic device is to be placed, wherein each of the one or more depictions shows the first structure of interest, a blood pool volume of a second anatomical structure of interest, or both;
   designating one or more positions in at least one of the one or more depictions wherein each position corresponds to a respective position in the first structure of interest at which the prosthetic device may be placed; and
   for each of the one or more designated positions, predicting an amount of blood flow obstruction through the second structure of interest that would be caused if the prosthetic device was to be placed at a corresponding position in the first structure of interest.

2. The method of claim 1, further comprising determining a position at which to place the prosthetic device within the first structure of interest based on the predicted blood flow obstruction through the second structure of interest.

3. The method of claim 1, wherein the one or more acquired depictions comprise(s) one or more computer-generated models.

4. The method of claim 1, wherein the one or more acquired depictions comprise(s) one or more images.

5. The method of claim 1, wherein for a given designated position, the predicting step comprises:
   determining a cross-sectional surface area of the blood pool volume of the second structure of interest following the designation of the given position; and
   predicting the blood flow obstruction based on the determined cross-sectional surface area.

6. The method of claim 1, wherein:
   the designating step comprises importing one or more models of the prosthetic device into at least one of the one or more acquired depictions; and
   the predicting step comprises predicting, for each of one or more positions of the one or more models of the prosthetic device in the at least one of the one or more acquired depictions, an amount of blood flow obstruction through the second structure of interest that would be caused if the prosthetic device was to be placed at a corresponding position in the first structure of interest.

7. The method of claim 6, wherein the at least one of the one or more depictions shows the first structure of interest and the blood pool volume of the second structure of interest, and the predicting step comprises:
   defining a plane that contains the aortic annulus of the patient's heart ("the aortic plane");
   offsetting a representation of the aortic plane to a point in the at least one of the one or more acquired depictions at which a portion of one of the one or more imported device models intersects the blood pool volume;
   determining a cross-sectional area of the blood pool volume along the offset representation of the aortic plane; and
   predicting the obstruction of the blood flow through the second structure of interest based on the determined cross-sectional area.

8. A system for evaluating the placement of a prosthetic device in a patient's body, comprising:
an electronic processor; and
an electronic memory device having instructions stored therein,
wherein the processor is configured to access the memory device and execute the instructions stored therein such that it is configured to:
acquire one or more depictions of an anatomical region of interest of the patient's body that includes a first anatomical structure of interest in which the prosthetic device is to be placed, wherein each of the one or more depictions shows the first structure of interest, a blood pool volume of a second anatomical structure of interest, or both;
designate one or more positions in at least one of the one or more depictions wherein each position corresponds to a respective position in the first structure of interest at which the prosthetic device may be placed; and
for each of the one or more designated positions, predict an amount of blood flow obstruction through the second structure of interest that would be caused if the prosthetic device was to be placed at a corresponding position in the first structure of interest.

9. The system claim 8, wherein the processor is further configured to determine a position at which to place the prosthetic device within the first structure of interest based on the predicted blood flow obstruction through the second structure of interest.

10. The system of claim 8, wherein the one or more acquired depictions comprise(s) one or more computer-generated models.

11. The system of claim 8, wherein the one or more acquired depictions comprise(s) one or more images.

12. The system of claim 8, wherein for a given designated position, the processor is configured to predict the amount of blood flow obstruction through the second structure of interest by:
determining a cross-sectional surface area of the blood pool volume of the second structure of interest following the designation of the given position; and
predicting the blood flow obstruction based on the determined cross-sectional surface area.

13. The system of claim 8, wherein the processor is configured to:
designate the one or more positions in the at least one of the one or more depictions by importing one or more models of the prosthetic device into the at least one of the one or more acquired depictions; and
predict the amount of blood flow obstruction by predicting, for each of one or more positions of the one or more models of the prosthetic device in the at least one of the one or more acquired depictions, an amount of blood flow obstruction through the second structure of interest that would be caused if the prosthetic device was to be placed at a corresponding position in the first structure of interest.

14. The system of claim 13, wherein the at least one of the one or more depictions shows the first structure of interest and the blood pool volume of the second structure of interest, and the processor is configured to predict the amount of blood flow obstruction through the second structure of interest by:
defining a plane that contains the aortic annulus of the patient's heart ("the aortic plane");
offsetting a representation of the aortic plane to a point in the at least one of the one or more acquired depictions at which a portion of one of the one or more imported device models intersects the blood pool volume;
determining a cross-sectional area of the blood pool volume along the offset representation of the aortic plane; and
predicting the obstruction of the blood flow through the second structure of interest based on the determined cross-sectional area.

15. The system of claim 8, wherein the prosthetic device is a prosthetic mitral heart valve.

16. The system of claim 8, wherein the second structure of interest comprises the left ventricular outflow tract (LVOT) of the patient's heart.

17. A non-transitory, computer-readable storage medium storing instruction thereon that when executed by one or more electronic processors causes the one or more electronic processors to carry out the method of:
acquiring one or more depictions of an anatomical region of interest of the patient's body that includes a first anatomical structure of interest in which the prosthetic device is to be placed, wherein each of the one or more depictions shows the first structure of interest, a blood pool volume of a second anatomical structure of interest, or both;
designating one or more positions in at least one of the one or more depictions wherein each position corresponds to a respective position in the first structure of interest at which the prosthetic device may be placed; and
for each of the one or more designated positions, predicting an amount of blood flow obstruction through the second structure of interest that would be caused if the prosthetic device was to be placed at a corresponding position in the first structure of interest.

18. The computer-readable storage medium of claim 17, wherein the method carried out by the one or more electronic processors further includes determining a position at which to place the prosthetic device within the first structure of interest based on the predicted blood flow obstruction through the second structure of interest.

19. The computer-readable storage medium of claim 17, wherein the prosthetic device is a prosthetic mitral heart valve, and the second structure of interest comprises the left ventricular outflow tract (LVOT) of the patient's heart.

20. The computer-readable storage medium of claim 17, wherein for a given designated position, the predicting step comprises:
determining a cross-sectional surface area of the blood pool volume of the second structure of interest following the designation of the given position; and
predicting the blood flow obstruction based on the determined cross-sectional surface area.

* * * * *